(12) United States Patent
Lin et al.

(10) Patent No.: US 7,695,738 B2
(45) Date of Patent: *Apr. 13, 2010

(54) CARBOHYDRATE ENCAPSULATED NANOPARTICLES

(75) Inventors: Chun-Cheng Lin, Fung-Yuan (TW); Chia-Chun Chen, Taipei (TW); Yi-Chun Wu, Taipei (TW)

(73) Assignees: Academia Sinica, Taipei (TW); National Taiwan University, Taipei (TW); National Taiwan Normal University, Taipei (TW)

( * ) Notice: Subject to any disclaimer, the term of this patent is extended or adjusted under 35 U.S.C. 154(b) by 1261 days.

This patent is subject to a terminal disclaimer.

(21) Appl. No.: 10/782,076

(22) Filed: Feb. 19, 2004

(65) Prior Publication Data

US 2005/0130240 A1    Jun. 16, 2005

Related U.S. Application Data

(60) Provisional application No. 60/448,716, filed on Feb. 19, 2003.

(51) Int. Cl.
| | |
|---|---|
| *A61K 9/14* | (2006.01) |
| *A61K 9/16* | (2006.01) |
| *A61K 31/70* | (2006.01) |
| *A61K 33/24* | (2006.01) |
| *A61K 33/04* | (2006.01) |
| *A01N 43/04* | (2006.01) |
| *A01N 43/16* | (2006.01) |
| *A01N 59/02* | (2006.01) |

(52) U.S. Cl. .................. 424/489; 424/490; 424/649; 424/703; 514/23

(58) Field of Classification Search .................. 424/489, 424/490, 649; 514/23
See application file for complete search history.

(56) References Cited

U.S. PATENT DOCUMENTS

| 6,231,733 B1 | 5/2001 | Nilsson et al. |
| 6,369,206 B1 | 4/2002 | Leone et al. |
| 6,465,435 B1 | 10/2002 | Heerze et al. |
| 7,186,398 B2 * | 3/2007 | Andres et al. ............... 424/9.1 |
| 2005/0287552 A1* | 12/2005 | Lin et al. ...................... 435/6 |

FOREIGN PATENT DOCUMENTS

WO    WO 02/32404    * 4/2002

OTHER PUBLICATIONS

Lin et al., Selective Binding of MAnnose-Encapsulated Gold Nanoparticles to Type 1 Pili in *Escherichia coli*, 2002, J. Am. Chem. Soc., 124, pp. 3508-3509.*
de la Fuente et al. (Angew Chem 2001, 113 (12), 2317-2321).*
Lin et al. (JACS 2002, 124, 3508-3509).*

(Continued)

*Primary Examiner*—Ernst V Arnold
(74) *Attorney, Agent, or Firm*—Hsiu-Ming Saunders; Intellectual Property Connections, Inc.

(57) ABSTRACT

The present invention provides carbohydrate encapsulated nanoparticles. In particular, the present invention provides metallic nanoparticles (e.g. gold nanoparticles) that are encapsulated in biologically important carbohydrate molecules, such as sugars, sugar derivatives, P-blood group antigens and analogues thereof. The present invention also provides methods of employing these carbohydrate encapsulated nanoparticles in diagnostic and therapeutic applications.

15 Claims, 12 Drawing Sheets

*a* Keys: (a) Ac$_2$O, pyr. DMAP, 90%. (b) HBr/HOAc, 80%. (c) 4-pentenyl alcohol, Hg(CN)$_2$, 88% (d) HSAc, AIBN, dioxane, 80%. (e) NaOMe (cat.), MeOH, 97%. (f) HAuCl$_4$, NaBH$_4$.

OTHER PUBLICATIONS

Benhamou (Colloidal Gold 1989 Academic Press, Inc, Sand Diego, CA chapter 4 pp. 95-141).*

Sandvig et al. (The Journal of Cell Biology 1989, 108, 1331-1343).*

Lanza et al., "In vivo molecular imaging of stretch-induced tissue factor in carotid arteries with ligand-targeted nanoparticles," J. Am. Soc. Echocardiogr., June; 13(6):608-14, 2000.

Hall et al., "Time evolution of enhanced ultrasonic reflection using a fibrin-targeted nanoparticulate contrast agent," J. Acoust. Soc. Am., Dec, 108(6):3049-57, 2000.

Kitov et al., "Shiga-like toxins are neutralized by tailored multivalent carbohydrate ligands," Nature, 403:669-672, 2000.

Sato, T., Ruth, R. Stabilization of Colloidal Dispersions by Polymer Adsorptions; Surfactants Science Series, No. 9; Marcel Dekker: New York, 1980, pp. 65-119.

A. Ulman, "Formation and Structure of Self-Assembled Monolayers," Chem. Rev., 96:1533-1554 [1996].

de la Fuente et al., "Gold Glyconanoparticles as Water-Soluble Polyvalent Models to STudy Carbohydrate Interactions," Angew. Chem. Int., 2001, 40(12):2258-61.

Otsuka et al., "Quantitative and reversible lectin-induced association of gold nanoparticles modified with alpha-lactosyl-omega-mercaptopoly(ethylene glycol)," J. Am. Chem. Soc., 2001, 123:8226-30.

Brust et al., "Synthesis of Thiol-derivatised Gold Nanoparticles in a Two-phase Liquid-Liquid System," J. Chem. Soc. Chem. Commun., 1994, 801-802.

Martinez et al., "Type 1 pilus-mediated bacterial invasion of bladder epithelial cells," EMBO J. Jun. 15, 2000;19(12):2803-12.

Stahl et al., "Beta 2-agonists administered by a dry powder inhaler can be used in acute asthma," Respir Med. Feb. 1998;92(2):167-72.

Lin et al., "Selective Binding of Mannose-Encapsulated Gold Nanoparticles to Type 1 Pili in *Escherichia coli*," JACS, 123:3805-3509 (2002).

Kartha et al., "A Simplified, One-Pot Preparation of Acetobromosugars From Reducing Sugars," J. Carbohydrate Chemistry, 9(5)777:781 (1990).

Keating et al., "Protein: Colloid Conjugates for Surface Enhanced Raman Scattering: Stability and Control of Protein Orientation," J Phys. Chem. 102:9404-9413 (1998).

Buskas et al., "Use of n-pentenyl glycosides as precursors to various spacer functionalities," J Org Chem. Feb. 25, 2000;65(4):958-63.

Neimeyer, Nanoparticles, Proteins, and Nucleic Acids: Biotechnology Meets Materials Science, Angew. Chem. Int. Ed, 40:4128-4158 (2001).

Mann et al., "Probing Low Affinity and Multivalent Interactions with Surface Plasman Resonance: Ligands for Concanavalin A," JACS 120(41)10575-10582 (1998).

Gestwicki et al., "Inter-receptor communication through arrays of bacterial chemoreceptors," Letter to Nature, 415:81-84 (2002).

Liang et al., "Measuring the forces involved in polyvalent adhesion of uropathogenic *Escherichia coli* to mannose-presenting surfaces," PNAS U S A. Nov. 21, 2000;97(24):13092-6.

Kingery-Wood et al., "The Agglutination of Erythrocytes by Influenza Virus is Strongly Inhibited by Liposomes Incorporating an Analog of Sialyl Gangliosides," JACS 114:7303-7305 (1992).

Lee et al., "A facile synthesis of 2-O-(alpha-D-mannopyranosyl)-alpha-D-mannopyranosides," Carbohydr Res. Jul. 10, 1995;271(1):131-6.

Bruchez et al., "Semiconductor nanocrystals as fluorescent biological labels," Science. Sep. 25, 1998;281(5385):2013-6.

Chan et al., "Quantum dot bioconjugates for ultrasensitive nonisotopic detection," Science. Sep. 25, 1998;281(5385):2016-8.

Lin et al., "Quantitative analysis of multivalent interactions of carbohydrate-encapsulated gold nano paraticles with concanavalin A," Chem Commun (Camb). Dec. 7, 2003;(23):2920-1.

Stahl, P. and Ezekowitz, R., "The mannose receptor is a pattern recognition receptor involved in host defense", Current Opinions in Immunology, vol. 10, pp. 50-55 (1998).

* cited by examiner

*Keys: (a) Ac$_2$O, pyr. DMAP, 90%. (b) HBr/HOAc, 80%. (c) 4-pentenyl alcohol, Hg(CN)$_2$, 88% (d) HSAc, AIBN, dioxane, 80%. (e) NaOMe (cat.), MeOH, 97%. (f) HAuCl$_4$, NaBH$_4$.

Typical TEM images of sectioned areas of (A) pili of the *E. coli* ORN178 strain bound with m-AuNP, (B) the *E. coli* ORN208 strain deficient of the *fimH* gene without m-AuNP binding. The experiments were performed in LB at room temperature. Scale bar = 100 nm.

A.

B.

A.

B.

CARBOHYDRATE ENCAPSULATED NANOPARTICLES

The present Application claims priority to U.S. Provisional Application Ser. No. 60/448,716, filed Feb. 19, 2003, which is herein incorporated by reference.

FIELD OF THE INVENTION

The present invention relates to carbohydrate encapsulated nanoparticles. In particular, the present invention relates to metallic nanoparticles (e.g. gold nanoparticles) that are encapsulated in biologically important carbohydrate molecules, such as sugar molecules, sugar derivatives, P-blood group antigens and analogues thereof. The present invention also relates to methods of employing these carbohydrate encapsulated nanoparticles in diagnostic and therapeutic applications.

BACKGROUND OF THE INVENTION

Basic scientific disciplines such as chemistry, biology, physics, and materials engineering are evolving and merging into interdisciplinary efforts in applied materials research, nanosciences, and molecular biotechnology. The aim of efforts is to develop advanced nanoparticles for use in a variety of emerging technical and biomedical fields. Recently, metallic, semiconducting, and magnetic nanoparticles have been developed through these efforts that are tailored to applications in electronics, optics, biotechnology, pharmaceutical and biomedical applications as well as for continued investigation in materials research and nanosciences.

The development of nanoparticles is typically conducted using bottom-up molecular design and fabrication methods (e.g., chemical synthesis and molecular self-assembly) rather than top-down methods (e.g., miniaturization). Bottom-up design and fabrication methods focus on creating increasingly larger functional systems from self-assembling molecules and colloidal building blocks. Typically, molecules used in bottom-up design and fabrication methods are selected based on their ability to provide distinct intrinsic functionality, such as steric, optical, electronic, catalytic properties, etc. The molecules should also have predictable tendencies in their specific constitution, configuration, and dynamic properties to ensure specific self-recognition and self-assembly.

For example, large quantities of inorganic nanoparticles can be prepared from various materials by relatively simple methods. The dimension and size distribution of these particles is optimally controlled within fairly narrow ranges. The most common materials used for producing nanoparticles include metals (e.g., Au), metal oxides, semiconductor materials (e.g., $Ag_2S$, CdS, CdSe, and $TiO_2$), and certain polymeric materials. The properties of metallic nanoparticle arrays depends on the size and shape of the colloidal particles they are made from as well as on their spatial arrangement.

Recently, improved understanding of the chemical and physical properties of nanoparticles has allowed researchers to fabricate nanoparticles with specific biocharacteristics and biofunctional groups. Researchers have used advanced recombinant biotechnology techniques to design and fabricate biofunctional groups such as, nucleic acids, proteins, carbohydrate ligands, and supramolecular complexes from the these components, suitable for attachment to organic and inorganic nano-, micro-, and mesoscopic scale particles. The attachment of biomacromolecular assemblies to nanoparticles provides a strong potential for the development of novel inorganic materials useful for biosensing, electronics, information processing, and catalytic applications.

Despite advances in nanoparticle design and fabrication, the emerging nanoparticles field still has many problems to overcome. For example, various problems exist in the fabrication of inorganic nanoparticles, including, degradation and inactivation of sensitive biological compounds due to harsh reaction conditions, and unpredictable ligand-exchange reactions that occur at colloid surfaces that hinder the formation of stable bioconjugates. Additionally, the synthesis of stoichiometrically defined nanoparticle-biomolecule complexes is very challenging. Thus, there remains a need for sensitive and low cost biofunctionalized nanoparticle based biosensors for a number of medically important analytes such as cell surface (e.g., bacteria adhesions) ligands.

SUMMARY OF THE INVENTION

The present invention provides carbohydrate encapsulated nanoparticles. In particular, the present invention provides metallic nanoparticles (e.g. gold nanoparticles) that are encapsulated in biologically important carbohydrate molecules, such as sugar molecules, sugar derivatives, P-blood group antigens and analogues thereof. The present invention also provides methods of employing these carbohydrate encapsulated nanoparticles in diagnostic and therapeutic applications.

In some embodiments, the present invention provides methods for treating a disease comprising; a) providing; i) a subject containing targets associated with the disease; and ii) a composition comprising a plurality of carbohydrate encapsulated nanoparticles, wherein each the carbohydrate encapsulated nanoparticles comprise a core metallic nanoparticle and a plurality of carbohydrate molecules configured to bind the targets, b) administering the composition to the subject under conditions such that the carbohydrate encapsulated nanoparticles bind the targets in the subject thereby reducing or eliminating the symptoms of the disease. In some embodiments, the subject has a disease selected from a urinary tract infection, hemolytic uremic syndrome ("HUS") and thrombotic thrombocytopenic purpura ("TTP").

In certain embodiments the present invention provides methods for detecting a target in a sample, comprising; a) providing; i) a composition comprising a plurality of carbohydrate encapsulated nanoparticles, wherein each of the carbohydrate encapsulated nanoparticles comprise a core nanoparticle (e.g. metallic) and a plurality of carbohydrate molecules configured to bind the target molecule, and ii) a test sample suspected of containing the target; b) contacting the composition with the test sample, and c) detecting the presence or absence of the target in the sample.

In particular embodiments, the carbohydrate encapsulated nanoparticles of the present invention are used as contrast reagents in vivo (e.g. for tissue imaging and other diagnostic techniques). In some embodiments the present invention provides methods for imaging tissue in a subject, comprising; a) providing; i) a composition comprising a plurality of carbohydrate encapsulated nanoparticles, wherein each of the carbohydrate encapsulated nanoparticles comprise a core nanoparticle (e.g. metallic) and a plurality of carbohydrate molecules configured to bind a particular tissue type (or organ or cell type, etc.), and ii) a subject; b) administering the composition to the subject, and c) imaging the tissue type in the subject. In certain embodiments, the imaging is acoustic or supersonic type imaging (See, e.g., Lanza et al., J. Am. Soc. Echocardiogr., June; 13(6):608-14, 2000; and Hall et al., J.

Acoust. Soc. Am., December, 108(6):3049-57, 2000; both of which are specifically incorporated by reference, including, for example, the teachings in these references regarding methods for imaging the nanoparticles in vivo).

In some embodiments, the present invention provides compositions comprising a plurality of carbohydrate encapsulated nanoparticles, wherein each of the carbohydrate encapsulated nanoparticles comprises a core metallic nanoparticle about 4-8 nm in diameter and plurality of carbohydrate molecules, wherein the plurality of carbohydrate molecules comprises at least 150 carbohydrate molecules.

In other embodiments, the present invention provides compositions comprising a plurality of carbohydrate encapsulated nanoparticles, wherein each of the carbohydrate encapsulated nanoparticles comprises a core metallic nanoparticle and a plurality of carbohydrate molecules, wherein the plurality of carbohydrate molecules comprises at least 150 carbohydrate molecules, and wherein the plurality of carbohydrate molecules are selected from the group consisting of mannose molecules and mannose derivative molecules.

In particular embodiments, the compositions of the present invention further comprise an aqueous solution, wherein the plurality of carbohydrate-encapsulated nanoparticles are present in a non-aggregated state in the aqueous solution. In other embodiments, the aqueous solution has high ionic strength. In additional embodiments, the plurality of carbohydrate molecules are selected from the group consisting of: mannose molecules, mannose molecule derivatives, glucose molecules and galactose molecules.

In certain embodiments, the present invention provides methods of detecting a target in a sample, comprising; a) providing; i) a composition comprising a plurality of carbohydrate encapsulated nanoparticles, wherein each of the carbohydrate encapsulated nanoparticles comprises a core metallic nanoparticle and a plurality of carbohydrate molecules, wherein the plurality of carbohydrate molecules comprises at least 150 carbohydrate molecules, and wherein the plurality of carbohydrate molecules are selected from the group consisting of mannose molecules and mannose derivative molecules, and ii) a test sample suspected of containing the target; b) contacting the composition with the test sample, and c) detecting the presence or absence of the target in the sample.

In some embodiments, the core nanoparticle comprises gold, platinum, zinc, copper, or silver, or combinations thereof. In certain embodiments, the carbohydrate encapsulated nanoparticle is about 0.1 nm to about 15 nm in diameter (e.g. 0.1 to 25 nm in diameter), or about 2-9 nm in diameter, or 4-8 nm in diameter. In preferred embodiments, the carbohydrate encapsulated nanoparticle is about 6 nm in diameter. In certain embodiments, the plurality of carbohydrate molecules consists of about 50-500 carbohydrate molecules (per core nanoparticle) or about 150-250 carbohydrate molecules, or about 200 carbohydrate molecules.

In certain embodiments, the carbohydrate encapsulated nanoparticles are non-aggregating (e.g. as viewed with a TEM, these nanoparticles are not aggregated together, and do not spontaneously aggregate). In some embodiments, the composition further comprises a high concentration of salt (e.g., $Na^+$, $Ca^{++}$, $Mg^{++}$), or has a high ionic strength (e.g. 0.3M) or a pH of 1.5 to 12.0, and is still not aggregated and is dissolveable in aqueous solution.

In some embodiments, the test sample contains the target molecule, and an additional candidate compound is combined with the test sample and carbohydrate encapsulated nanoparticle. It is then determined if the candidate compound interferes with the binding of the target with the nanoparticle (e.g. a screen for antagonist compounds).

In certain embodiments, the plurality of carbohydrate molecules are sugar molecules or sugar derivatives. In particular embodiments, the plurality of carbohydrate molecules are monosaccharides (e.g. mannose or mannose derivative). In other embodiments, the plurality of carbohydrate molecules are dissacharides.

In particular embodiments, the plurality of carbohydrate molecules are thiolated. In certain embodiments, the plurality of carbohydrate molecules comprise mannose molecules or derivatives of mannose molecules. In some embodiments, the target is a bacteria comprising a type I pili (e.g. E. coli). In some embodiments, the target comprises a FimH molecule (e.g. recombinantly expressed FimH, which may be attached to a solid support). In additional embodiments, the target comprises a cell expressing a mannose receptor or a purified mannose receptor molecule.

In some embodiments, the plurality of carbohydrate molecules comprises P-blood group antigens or analogs thereof (e.g. galabiose, Pk, P, or Forssman, or combinations therof, or analogs thereof). In preferred embodiments, the plurality of carbohydrate molecules comprise the Pk antigen or an analog thereof. In certain embodiments, the plurality of carbohydrate molecules comprise the STARFISH molecule shown in FIG. 1 of Kitov et al., Nature, 403:669-672, 2000, herein incorporated by reference in its entirety. In particular, FIG. 1 from Kitov et al. is specifically herein incorporated by reference.

In further embodiments, the target comprises bacteria comprising type P-pili (e.g. uropathogenic E. coli). In some embodiments, the target comprises PapG molecules (e.g. recombinantly expressed PapG molecules, which may be attached to a solid support). In particular embodiments, the target comprises S. suis bacteria. In other embodiments, the target comprises E. coli verotoxin. In additional embodiments, the target comprises a plurality of candidate carbohydrate binding partners (e.g. library of synthetically generated proteins or carbohydrates, etc.).

In some embodiments, the carbohydrate encapsulated nanoparticles further comprise a detectable label. In certain embodiments, the label is a fluorescent, radioactive, or enzymatic moiety. In certain embodiments, labeled carbohydrate encapsulated nanoparticles are used for in vivo imaging of a subject (e.g. human patient). In some embodiments, the carbohydrate encapsulated nanoparticles are labeled with radioisotopes and the nanoparticles are used for radiation therapy (e.g. to treat various types of cancers).

In some embodiments, the present invention provides compositions comprising a gold core nanoparticle encapsulated by a plurality of P-blood group antigen molecules or P-blood group antigen analogs. In certain embodiments, the plurality of P-blood group antigen molecules comprise Pk antigen molecules or analogs thereof. In some embodiments, the P-blood group antigens are thiolated.

In some embodiments, the present invention provides kits comprising i) a composition comprising a plurality of carbohydrate encapsulated nanoparticles, wherein each of the carbohydrate encapsulated nanoparticles comprise a core nanoparticle (e.g. metallic) and a plurality of carbohydrate molecules configured to bind a target molecule, and ii) instructions for using the carbohydrate encapsulated nanoparticles (e.g. instructions for therapeutic, diagnostics, or basic research use). In further embodiments, the kits further comprises a control target known to bind to the carbohydrate encapsulated nanoparticles. In other embodiments, the nanoparticles in the kits are configured for detecting molecules indicative of pregnancy. In further embodiments, the nanoparticles are incorporated into a device, such as a pregnancy device.

DEFINITIONS

Figure 1:
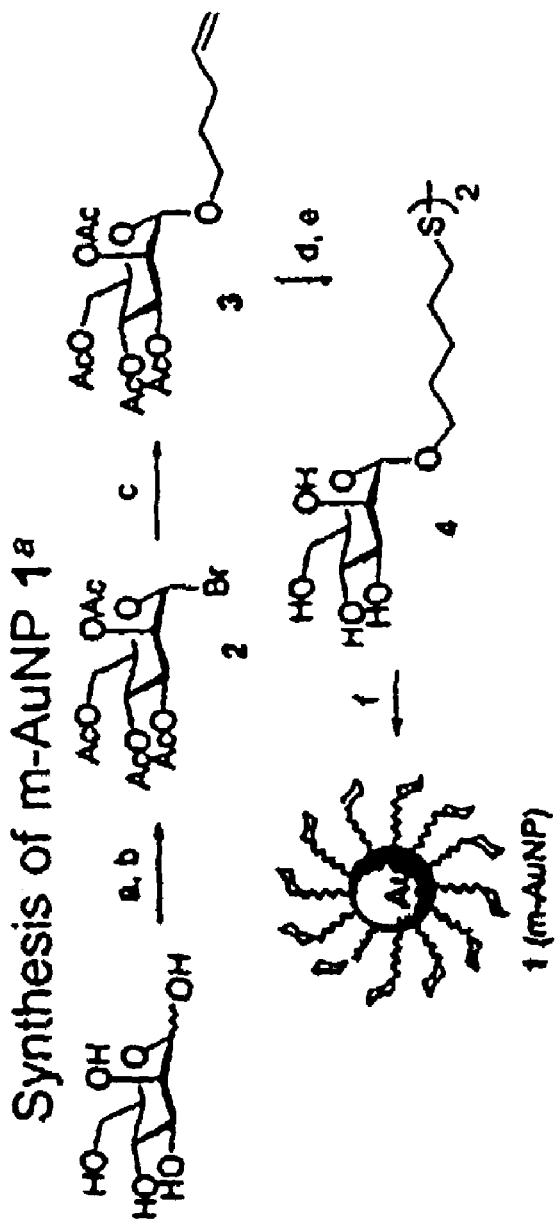
FIG. 1 shows a schematic representation of one method for generating mannose encapsulated gold nanoparticles. The legend to this figures is as follows: (a) $Ac_2O$, pyr. DMAP, 90%; (b) HBr/HOAc, 80%; (c) 4-pentenyl alcohol, $Hg(CN)_2$, 88%; (d) HSAc, AIBN, dioxane, 80%; (e) NaOme (cat.), MeOH, 97%; (f) $HAuCl_4$.

To facilitate an understanding of the invention, a number of terms are defined below.

As used herein, the terms "subject" and "patient" refer to any animal, such as a mammal like a dog, cat, bird, livestock (e.g. pig), and preferably a human.

The term "sample" and "test sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "test compound" or "candidate compound" refer to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "response," when used in reference to an assay, refers to the generation of a detectable signal (e.g., accumulation of reporter protein, increase in ion concentration, accumulation of a detectable chemical product).

The term "signal" as used herein refers to any detectable effect, such as would be caused or provided by a label or an assay reaction.

As used herein, the term "detector" refers to a system or component of a system, e.g., an instrument (e.g. a camera, fluorimeter, charge-coupled device, scintillation counter, optical microscope, optical spectroscope, tunneling electron microscopre (TEM), etc.) or a reactive medium (X-ray or camera film, pH indicator, etc.), that can convey to a user or to another component of a system (e.g., a computer or controller) the presence of a signal or effect. A detector can be a photometric or spectrophotometric system, which can detect ultraviolet, visible or infrared light, including fluorescence or chemiluminescence; a radiation detection system; a spectroscopic system such as nuclear magnetic resonance spectroscopy, mass spectrometry or surface enhanced Raman spectrometry; a system such as gel or capillary electrophoresis or gel exclusion chromatography; or other detection systems known in the art, or combinations thereof.

As used herein, the term "nanoparticle" refers to small particles (e.g. micrometer range) that effectively serve as a solid support or solid phase for chemical reactions (e.g. capture reagent binding to a target). Even though particles can be of any size, the preferred size is 0.001-500 μm, more preferably 0.01-10 μm, even more preferably 0.5-8.0 μm, and most preferably approximately 6.0 μm in diameter. The particles may be uniform (e.g., being about the same size) or of variable size. Particles may be any shape (e.g. spherical or rod shaped), but are preferably made of regularly shaped material (e.g. spherical).

As used herein, the term "target" refers to a molecule, cell, or other biological material in a sample to be detected or targeted by nanoparticles. Examples of target molecules include, but are not limited to, cell surface ligands, cells in a subject, pathogens, such as bacteria and viruses, antibodies, naturally occurring drugs, synthetic drugs, pollutants, allergens, affector molecules, growth factors, chemokines, cytokines, and lymphokines.

As used herein the term "encapsulated" when used in reference to nanoparticles and carbohydrates refers to a configuration where a nanoparticle (e.g. a gold nanoparticle) has carbohydrate molecules attached thereto throught covalent and non-covalent bonds, such that the carbohydrate molecules are approximately evenly distributed around about the entire surface of the nanoparticle.

The term "label" as used herein refers to any atom or molecule that can be used to provide a detectable (preferably quantifiable) effect and that can be attached to a nanoparticle. Labels include but are not limited to dyes; radiolabels such as $^{32}P$; binding moieties such as biotin; haptens such as digoxigenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction, TEM, or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral.

DESCRIPTION OF THE INVENTION

The present invention provides carbohydrate encapsulated nanoparticles. In particular, the present invention provides metallic nanoparticles (e.g. gold nanoparticles) that are encapsulated in biologically important carbohydrate molecules, such as sugars, sugar derivatives, P-blood group antigens and analogues thereof. The present invention also provides methods of employing these carbohydrate encapsulated nanoparticles in diagnostic and therapeutic applications.

The carbohydrate encapsulated nanoparticles of the present invention, are particularly gold carbohydrate encapsulated nanoparticles, are well suited for biological applications. Previous reports have shown that gold nanoparticles stabilized by surfactants or polymers were not effective in preventing aggregation of the nanoparticles, particularly under high concentrations of salt medium (See, Sato, T., Ruth, R. *Stabilization of Colloidal Dispersions by Polymer Adsorptions*; Surfactants Science Series, No. 9; Marcel Dekker: New York, 1980, pp 65-119). In contrast, the carbohydrate encapsulated gold particles of the present invention were found to be very stable in deonized water and phosphate buffered solution (PBS), and their stability was independent of high ion strength and pH values in the range from 1.5 to 12 of solutions. Moreover, the carbohydrate encapsulated gold particles of the present invention were easily redissolved in aqueous media without aggregation.

The carbohydrate encapsulated nanoparticles also address the problem of weak binding strength of individual carbohydrate-lectin interactions, making them useful for both diagnostic and therapeutic applications. In nature, the individually weak carbohydrate-lectin interactions may be compensated for by multivalent interactions. It has been found that presenting the carbohydrate in a multivalent manner increases binding much more than could be expected from the increase in carbohydrate concentration. This is called the "multivalent effect," which has also been shown to increase recognition specificity. The carbohydrate encapsulated molecules of the present invention allow the desired carbohydrate to be presented in a multivalent fashion (e.g. 100-300 carbohydrate molecules per gold particle), thus benefiting from the multivalent effect (thereby having high levels of avidity to compensate for what may otherwise low levels of affinity).

The remainder of the description of the invention is provided below in the following sections: I. Carbohydrate encapsulated nano-particles; II. Screening assays and arrays; and III. Carbohydrate encapsulated nanoparticle therapy.

I. Carbohydrate Encapsulated Nanoparticles

The present invention provides carbohydrate encapsulated nanoparticles. These particles may be generated with any type of carbohydrate attached to any type of nanoparticle, preferably a gold nanoparticle.

A. Nanoparticles

The core of the carbohydrate encapsulated nanoparticles of the present invention is a solid support in the micrometer size range. The nanoparticles employed to construct the carbohydrate encapsulated nanoparticles of the present invention are preferably small particles (e.g. micrometer range) that effectively serve as a solid support or solid phase for chemical reactions (e.g. capture reagent binding to a target) that may be immobilized on an array, used for in vivo and in vitro diagnostics, or employed in vivo in a therapeutic manner. Even though particles can be of any size, the preferred size is 0.001-500 µm, more preferably 0.01-100 µm, even more preferably 1.0-10.0 µm, and most preferably approximately 5-7.0 µm in diameter. The particles may be uniform (e.g., being about the same size) or of variable size (e.g. spherical or rod shaped). Particles may be any shape, but are preferably made of regularly shaped material (e.g. spherical).

Nanoparticles may be composed of any type of material, and are preferably composed of metal (e.g. gold). For example, the nanoparticles useful in the present invention may be composed of a metal (e.g., gold, silver, copper, platinum, lead, cadmium, indium, zinc, or combinations therof.), semiconducting material (e.g., CdSe, CdS, and CdS or CdSe coated with ZnS) or magnetic (e.g., ferromagnetite) colloidal materials. In preferred embodiments, the nanoparticles comprise metallic atoms. In other embodiments, particular materials useful in the practice of the invention include, but are not limited to, ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, GaAs, and $NiFe_2O_4$ nanoparticles. In particularly preferred embodiments, the nanoparticles comprise gold atoms (e.g. gold sphere and/or rods).

Methods of fabricating metallic, semiconducting, and magnetic nanoparticles are well-known in the art. (See e.g., G. Schmid, (ed.) Clusters and Colloids, VCH, Weinheim, [1994]; M. A. Hayat, (ed.) Colloidal Gold: Principles, Methods, and Applications (Academic Press, San Diego, [1991]); R. Massart, IEEE Taransactions On Magnetics, 17:1247 [1981]; T.S. Ahmadi et al., Science, 272:1924 [1996]; and A. C. Curtis et al., Angew. Chem. Int. Ed. Engl., 27:1530 [1988]), all of which are herein incorporated by reference. Methods of fabricating ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. (See e.g., Brus, Appl. Phys. A., 53:465 [1991]; Bahncmann, in Photochemical Conversion and Storage of Solar Energy (eds. Pelizetti and Schiavello 1991), p. 251; Wang and Herron, J. Phys. Chem., 95:525 [1991]; and Ushida et al., J. Phys. Chem., 95:5382 [1992]), all of which are herein incorporated by reference.

Suitable gold nanoparticles (or suitable gold nanoparticle precursors) are also commercially available from, for example, Ted Pella, Inc., (Redding, Calif.), Amersham Corporation (Piscataway, N.J.) and Nanoprobes, Inc., (Yaphank, N.Y.) among other sources. Generally, any method of nanoparticle fabrication (e.g., citrate reduction, vacuum synthesis, gas-phase synthesis, condensed phase synthesis, high speed deposition by ionized cluster beams, consolidation, high speed milling, mixalloy processing, deposition methods, ablation [with laser light] of bulk planar surfaces, and sol-gel methods) that produces suitable nanoparticles is within the scope of the present invention. However, in preferred embodiments, the core nanoparticle is formed such that the resulting particle is carbohydrate encapsulated (See below and Example 4).

Gold colloidal particles have high extinction coefficients and their characteristic spectral bands are often vibrant and easily distinguished. These spectral response of gold nanoparticles changes with particle size, concentration, interparticle distance, extent of aggregation and shape (geometry) of the aggregates, making these materials attractive for use in calorimetric and/or colorimetric assays. Those skilled in the art are capable of fabricating nanoparticles (e.g., gold nanoparticles) suitable for specific applications. Accordingly, the compositions and methods of the present invention are readily adaptable to encompass a number of embodiments not specifically recited herein with no more than routine experimentation. For example, spherical gold particles are usually reddish in color, while rod shaped gold particles tend to be purple or blue. As such, gold particles of different shapes containing different carbohydrates attached to their surface can be distinguished even in mixed populations. In this way multi-ligand assays can be run with mixtures of shapes and sizes of gold particles with varying carbohydrate molecules on their surface.

Gold nanoparticles are preferred for use in the nanofabrication of the devices (e.g., arrays) and compositions contemplated by the present invention for the reasons mentioned above, and because of their stability, ease of imaging by electron microscopy, and ready modification with thiol functionalities.

In still other embodiments, carbohydrate encapsulated nanoparticle compositions are suitable for use as probes in both LM and TEM immunocytochemistry, tissue imaging, etc. The present invention is not limited, however, to compositions and methods that rely on LM and/or TEM imaging techniques.

B. Carbohydrates

The nanoparticles of the present invention are encapsulated with a plurality of carbohydrates. The invention is not limited by the type of carbohydrate, or how it is functionalized in order to be combined with the core nanoparticle (e.g. carbohydrates may be thiolated, etc.).

Carbohydrates are generally considered aldehyde or ketone compounds with multiple hydroxyl groups. An approximate formula for carbohydrates is $(CH_2O)$, and for various values of X include sugars, starches and cellulose. The simple carbohydrates are mono-, di-or poly saccharides, having repeating units usually containing 5 or 6 carbon atoms joined through oxygen linkages. Examples of monosaccharides include glucose and mannose. Examples of disaccharides include, for example, sucrose and lactose. An example of a polysaccharide is cellulose, which is a polymer containing approximately 2000-3000 glucose units per molecule. The basic sugar skeleton of carbohydrates, involving hydroxyl groups, generally gives them properties such as water solubility and sweet taste. Also, as many carbon atoms are asymmetric, the carbohydrates can exist in many stereochemical and structural forms.

Sugars are a sub-class of carbohydrates that are aldehyde or ketone derivatives of polyhydric alcohols. The two principal groups of sugars are the disaccharides, having the formula $C_{12}H_{22}O_{11}$, and the monosaccharides, $C_6H_{12}O_6$, which are white, crystallizable solids, soluble in water and dilute in alcohol. Examples of monosaccharides include, but are not limited to, glyceraldehydes, erythrose, ribose, allose, altrose, arabinose, glucose, mannose, threose, xylose, gulose, idose, lyxose, galactose, talose, dihydroxyacetone, erythrulose, ribulose, psicose, fructose, xylulose, sorbose, tagatose, and D/L stereoisomers, enantiomers, anomers (e.g., α-D-glucopyranose, β-D-glucopyranose, etc.) phosphorylated derivatives. Examples of disaccharides include, but are not limited to, sucrose, lactose, and maltose.

i. Mannose and Mannose Derivatives

In preferred embodiments, the nanoparticles of the present invention are encapsulated in mannose molecules or mannose derivatives. The mannose molecules may in the open chain or cyclic forms. Mannose derivatives include, but are not limited to, 4-nitrophenylthiomannoside, phenyl mannoside, a-mannose, mannose 6-phosphate, mannose 1-phosphaste, GDP-mannose, as well as the those provided in the following references: Dupre et al., Bioorganic & Medicinal Chemistry Letters, vol. 6, no. 5, 1996 (pp. 569-572); Lin et al., Bioorg Med Chem, vol. 7, no. 3, 1999 Mar (pp. 425-33); Kogan et al., J Med Chem, vol. 38, no. 267 1995 Dec. 22 (pp. 4976-84), all of which are incorporated by reference. Preferably the mannose molecule or derivative is thiolated (See, e.g. FIG. 1, where a thio-mannosyle dimer is shown).

Also in preferred embodiments, the mannose molecule or derivative is such that it is capable of binding in vivo or in vitro to a mammalian mannose receptor (MR). In humans, the MR is a 180 kDa transmembrane protein (See Lennartz et al., J. Biol. Chem., 1988, 262:9942-9944 and Ezekowitz et al., J. Exp. Med. 1990, 172:1785-1794, both of which are incorporated by reference). Whether a particular mannose derivative binds MR can be determined by running a simple binding assay (e.g. using nanoparicles encapsulated in the candidate mannose derivative and MR molecules).

In other preferred embodiments, the mannose molecule or derivative is such that it is capable of binding in vivo or in vitro to type 1 *E. coli* pili via FimH. Again, whether a particular mannose derivative binds FimH can be determined by running a simple binding assay (e.g. using nanoparticles encapsulated in the candidate mannose derivative and FimH molecules).

ii. P-Blood Group Antigens and Analogues Thereof

Figure 7:
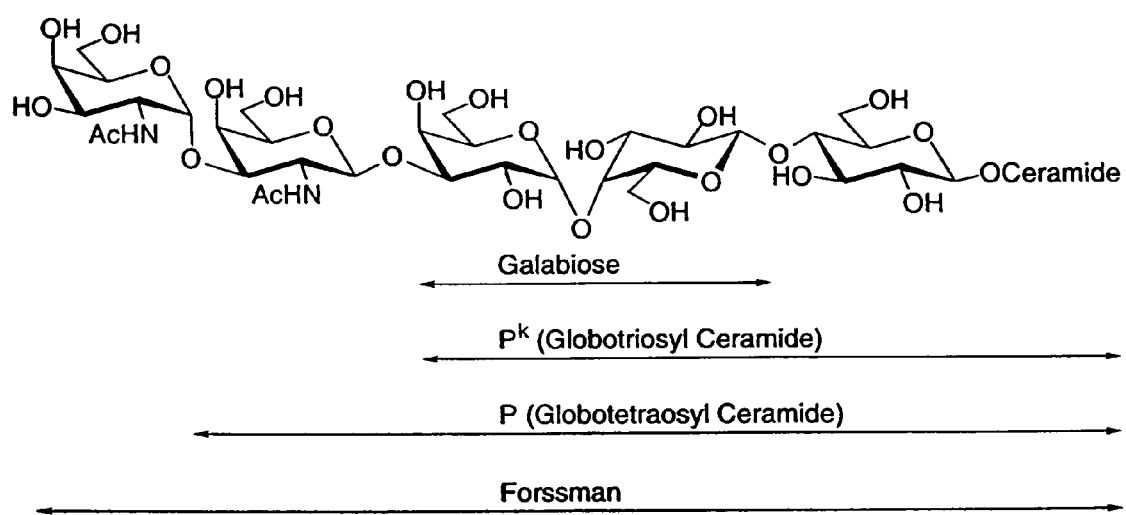
FIG. 7 shows the chemical structure of the core galabiose molecule, as well as the Pk antigen (globotriosyl ceramide), P (globotetraosyl ceramide), and Forssman.

In certain embodiments, the nanoparticles of the present invention are encapsulated in P-Blood group antigens or analogues thereof. In some embodiments, the P-blood group antigen is from the globoseries (e.g. P and Pk) or lactoseries (e.g. P1). The globoseries includes, for example, galabiose, Pk (globotriose or globotriosyl ceramide), P (globotetraosyl ceramide) and Forssman (See, e.g. FIG. 7). In some embodiments, the present invention employs P-blood group analogs.

The P antigen is present on all normal erythrocytes in humans, while Pk is more rare. Unlike other carbohydrates blood group antigen (e.g. ABO), which are presented as both glycolipids and glycoproteins, it appears that the P-blood group antigens are presented only as glycolipids.

P-blood group antigens are not only blood group antigens, but also have a role as cancer antigens. For example, P-blood group antigen are present on teratocarcinoma cells (Kannagi et al., J. Biol. Chem., 1983, 258:8934-42), embryonal carcinoma cells, (Fukuda et al., J. Biol. Chem. 1986, 261:5145-53) Burkitt's lymphoma (Lanne et al., Glycobiology, 1996, 6:423-32) and human myeloid leukemia cells (Kniep et al., J. Biochem. 1985, 149:187-91), and serve as tumor markers and are involved in certain adhession processes. The P-blood group antigens also serve as ligands for bacteria (e.g. Uropathogenic *E. coli*), *Streptococcus suis*, certain toxins (e.g. Shiga toxin from *Shigella dysenteria* and verotoxin from *E. coli*), and for viruses (e.g. parvovirus B19, responsible for a number of human diseases (See, Chipman et al., PNAS, 1996, 93:7502-6). All the above references are herein incorporated by reference.

In some embodiments, the carbohydrate is galabiose or an analog thereof. Various galabiose analogs are described, for example, in the following references: Kihlberg et al., J. Am. Chem. Soc., 1989, 111:6364-68; Magnusson et al., J. Meth. Enzymol. 1995, 253:105-114; and Nilsson et al., Bioorg. Med. Chem. 1996, 4:1809-17, all of which are herein incorporated by reference. In other embodiments, the carbohydrate is the Pk antigen or analogs thereof. Various Pk antigen analogs are described, for example, in the following references: Zhiyuan et al., Carbohydr. Res. 1994, 262:79-101; Zhang et al., J. Org. Chem. 1995, 60:7304-15; and Mylvaganam et al., Biochem. J. 2002, Dec. 15; 368 (PT3):769-76, all of which are herein incorporated by reference.

iii. Carbohydrate Based Drugs and Glycomics

In certain embodiments, the nanoparticles of the present invention are encapsulated in one or more carbohydrate based drugs (e.g. carbohydrate based drugs that are known or that are discovered through the emerging filed of glycomics). Glycomics is an emerging field that examines the role of carbohydrates in biological systems. This field seeks to do for sugars and carbohydrates what genomics and proteomics have done for genes and proteins. Toward this end, the National Institute of General Medical Sciences of the National Institute of Health has identified glycomics as one of the key fields that will shape the future of Molecular and Cellular Biology and has funded a Consortium for Functional Glycomics.

Until recently, researches believe carbohydrates merely functioned as energy sources and structural supports in biological systems. However, through new glycomics efforts, it is increasingly recognized that carbohydrates are complex molecules involved in many biological functions. In fact, carbohydrates have recently been identified as the most information dense structures in the body, controlling a multitude of intercellular and cell to tissue communications. As such, one of the aims of the glycomics efforts is to identify or design carbohydrates that fit receptor molecules as well as carbohydrates exploited by disease causing pathogens. In this regard, it is believed that the glycomics efforts will lead to new carobohydrate drugs, new drug targets, and improvements of existing drugs and a better understanding of pathogenic infections.

Glycomics research has lagged behind genetic and protein research as researchers lacked effective tools for studying carbohydrates. Part of the problem is the fact that carbohydrates are very complex, generally branched molecules, with more than 30 core components (compared to 4 for nucleic acids, and 20 for proteins). A second part of the problem is the fact that the first practical methods for sequencing and synthesizing sugars was only introduced a few years ago. These recent innovations should greatly expand the field of glycomics and hasten the development of new carbohydrate based therapeutics.

Carbohydrate therapeutics that are discovered through the new field of glycomics may be used to generate encapsulated nanoparticles (e.g. thiolate a new carbohydrate therapeutic and attach to gold nanoparticles). Importantly, the present invention allows these carbohydrates to be presented in a multivalent fashion (e.g. about 200 carbohydrate molecules per gold nanoparticle) such that the desired therapeutic effect may be achieved (e.g. since the binding of carbohydrate therapeutics to their targets may only be effective if presented in a multivalent form, with high avidity).

C. Methods of Making Carbohydrate Encapsulated Nanoparticles

Any type of method may be used to make carbohydrate encapsulated nanoparticles. In preferred embodiments, the core nanoparticles itself is gold and the plurality of carbohydrate molecules are thiolated (see e.g., See e.g., A. Ulman, Chem. Rev., 96:1533-1554 [1996], herein incorporated by reference). In preferred embodiments, the gold particles are made from ionic gold, such as $HAuCl_4$ (See Example 4). The ionic gold may be mixed with a solvent such as toluene in the presence of tetraoctylammonium (the organic layer may then be separated out). In some embodiments, a reducing agent (e.g. sodium borohydride) is added to the functionalized carbohydrate (e.g. thioloated carbohydrate). This mixture may then be added to the gold mixture, such that the reducing agent caused gold particles (encapsulated with the carbohydrate) to form. The carbohydrate encapsulated gold particles can then be removed from solution (e.g. by centrifugation) and dried (e.g. under a vacuum). Additional methods of making carbohydrate encapsulated gold nanoparticles are described, for example, in de la Fuente et al., Angew. Chem. Int., 2001, 40(12):2258-61; Otsuka et al., J. Am. Chem. Soc., 2001, 123:8226-30; Brust et al; J. Chem. Soc. Chem. Commun., 1994, 801-802; and U.S. Pat. No. 6,369,206 to Leone et al., all of which are herein incorporated by reference.

II. Carbohydrate Encapsulated Nanoparticle Therapy

The carbohydrate encapsulated nano-particles of the present invention find use in therapeutic applications. The solubility and multivant properties of the compositions of the present invention make them well suited for functioning as therapeutics. For example, the present invention provides novel methods of treating diseases characterized by pathogenic infection comprising administering a plurality of encapsulated gold nanoparticles to a subject in any sterile, biocompatible pharmaceutical carrier, including, but not limited to, saline, buffered saline, dextrose, and water.

In some embodiments, the methods of the present invention comprise administering carbohydrate encapsulated nanoparticles in a suitable pharmaceutical composition. In other embodiments, the pharmaceutical compositions contain a mixture of at least two types of encapsulated nanoparticles of similar or dissimilar type co-administered to a subject. In still further embodiments, the pharmaceutical compositions of the present invention comprise a plurality of encapsulated nanoparticles administered to a subject under one or more of the following conditions: at different periodicities, different durations, different concentrations, different administration routes, etc.

In some preferred embodiments, the compositions and methods of the present invention find use in treating diseases or altering physiological states characterized by undesirable cell migration, angiogenesis, or loss of apoptotic control (e.g., cancers). However, the present invention is not limited to ameliorating (e.g., treating) only these types of conditions in a subject. Indeed, various embodiments of the present invention are directed to treating a range of physiological symptoms and disease etiologies in a subject which are characterized by or arise by infection with a pathogen (e.g., bacteria, archeae, viruses, mycoplasma, fungi, etc.). Described below are certain preferred therapeutics uses, as well as formulations, for the carbohydrate encapsulated nanoparticles of the present invention.

A discussed further below, in preferred embodiments, the present invention provides carbohydrate encapsulated nanoparticles for treating *E. coli* infections. *Escherichia coli* is the organism most commonly isolated in clinical microbiology laboratories, as it is usually present as normal flora in the intestines of humans and other animals. However, it is an important cause of intestinal, as well as extraintestinal infections. For example, in a 1984 survey of nosocomial infections in the United States, *E. coli* was associated with 30.7% of the urinary tract infections, 11.5% of the surgical wound infections, 6.4% of the lower respiratory tract infections, 10.5% of the primary bacteremia cases, 7.0% of the cutaneous infections, and 7.4% of the other infections (J. J. Farmer and M. T. Kelly, "Enterobacteriaceae," in Manual of Clinical Microbiology, Balows et al.(eds), American Society for Microbiology, [1991], p. 365). Surveillance reports from England, Wales and Ireland for 1986 indicate that *E. coli* was responsible for 5,473 cases of bacteremia (including blood, bone marrow, spleen and heart specimens); of these, 568 were fatal. For spinal fluid specimens, there were 58 cases, with 10 fatalities (J. J. Farmer and M. T. Kelly, "Enterobacteriaceae," in Manual of Clinical Microbiology, Balows et al. (eds), American Society for Microbiology, [1991], p. 366).

Studies in various countries have identified certain serotypes (based on both the O and H antigens) that are associated with the four major groups of *E. coli* recognized as enteric pathogens. Table 1 lists common serotypes included within these groups. The first group includes the classical enteropathogenic serotypes ("EPEC"); the next group includes those that produce heat-labile or heat-stable enterotoxins ("ETEC"); the third group includes the enteroinvasive strains ("EIEC") that mimic *Shigella* strains in their ability to invade and multiply within intestinal epithelial cells; and the fourth group includes strains and serotypes that cause hemorrhagic colitis or produce Shiga-like toxins (or verotoxins).

Most strains of uropathogenic *E. coli* (UPEC) encode filamentous adhesive organelles called type 1 pili. Type 1 pili are composed of FimA, FimF, FimG, and FimH proteins. FimA accounts fro more than 98% of the pilus protein, and FimH is uniquely responsible for the binding to D-mannose.

EPEC use the ability to bind mannose (via FimH) in the infection process. For example, EPEC are implicated in over 80% of all urinary tract infections (UTIs), infections that are mediated by type I pili. It has been determined that *E. coli* bind mannose in the urinary tract via mannose, and further that the invasion of the *E. coli* cells in human bladder epithelial cells is mediated via mannose attachment (See, Martines, et al., EMBO, 19:2803-12; 2000, herein incorporated by reference). As such, administering mannose encapsulated nanoparticles to a subject infected with EPEC (e.g. a subject with a UTI) could be used to treat the infection by preventing the EPEC from binding to and infiltration cells of the subject.

B. Therapeutic Uses of P-Blood Group Encapsulated Nanoparticles

The present invention provides P-Blood group antigen (and P-blood group antigen analog) encapsulated nanoparticles. These nanoparticles are useful, for example, as agents to disrupt the binding of bacteria (e.g. uropathogenic *E. coli*, and *S. suis*), bacterial toxins (e.g. Shiga toxin or verotoxin) and viruses (e.g. parvovirus B19) to P-blood group antigens in a host. These nanoparticles may also be used to visualize

TABLE 1

Pathogenic *E. coli* Serotypes

| Group | Associated Serotypes |
|---|---|
| Enterotoxigenic: | O6:H16; O8:NM; O8:H9; O11:H27; O15:H11; O20:NM; O25:NM; O25:H42; O27:H7; O27:H20; O63:H12; O78:H11; O78:H12; O85:H7; O114:H21; O115:H21; O126:H9; O128ac:H7; O128ac:H12; O128ac:H21; O148:H28; O149:H4; O159:H4; O159:H20; O166:H27; and O167:H5 |
| Enteropathogenic: | O26:NM; O26:HI1; O55:NM; O55:H6; O86:NM; O86:H2; O86:H34; O111ab:NM; O111ab:H2; O111ab:H12; O111ab:H21; O114:H2; O119:H6; O125ac:H21; O127:NM; O127:H6; O127:H9; O127:H21; O128ab:H2; O142:H6; and O158:1123 |
| Enteroinvasive: | O28ac:NM; O29:NM; O112ac:NM; O115:NM; O124:NM; O124:H7; O124:H30; O135:NM; O136:NM; O143:NM; O144:NM; O152:NM; O164:NM; and O167:NM |
| Verotoxin-Producing | O1:NM; O2:H5; O2:H7; O4:NM; O4:H10; O5:NM; O5:H16; O6:H1; O18:NM; O18:H7; O25:NM; O26:NM; O26:H11; O26:H32; O38:H21; O39:H4; O45:H2; O50:H7; O55:H7; O55:H10; O82:H8; O84:H2; O91:NM; O91:H21; O103:H2; O111:NM; O111:H8; O111:H30; O111:H34; O113:H7; O113:H21; O114:H48; O115:H10; O117:H4; O118:H12; O118:H30; O121:NM; O121:H19; O125:NM; O125:H8; O126:NM; O126:H8; O128:NM; O128:H2; O128:H8; O128:H12; O128:H25; O145:NM; O125:H25; O146:H21; O153:H25; O157:NM; O157:H7; O163:H19; O165:NM; O165:19; and O165:H25 |

The present invention provides compositions for treating infections caused by *E. coli*, and in particular, the serotypes listed in table 1.

A. Therapeutics Uses For Mannose Encapsulated Nanoparticles

The present invention provides mannose (and mannose derivative) encapsulated nanoparticles. These nanoparticles are useful, for example, as agents to disrupt the binding of bacteria to mannose molecules in a host, as well as binding to mannose receptors in a subject. These nanoparticles may also be used to visualize the presence of bacteria in a subject in order to provide a diagnostic read out.

Type 1 pili are filamentous proteinaceous appendages that extend from the surface of many gram-negative organisms.

the presence of bacteria, toxins, and viruses in a subject in order to provide a diagnostic read out.

Uropathogenic *E. coli* (UPEC) also have P-pili on their surface that help mediate urinary tract infections. Generally, for urinary tract infections, the urethra and bladder are infected, but in more severe cases the infection can reach the kidneys (pyelonephritis). Infection of the kidneys increases the risk of a blood stream infection and can lead to meningitis. The first step in the UPEC infection process is mediated by the pili of the *E. coli*. One type of pili employed is the P-pili that are generally composed of PapA, but are also composed of PapG. PapG allows the *E. coli* to bind the disaccharide galabiose and prevents the bacteria from being flushed from the body. As such, nanoparticles encapsulated in galabiose or an analog thereof could be useful in treating UTI infections and preventing more serious disease consequences.

*Streptococcus suis* is a Gram positive bacteria that may cause menigitis in humans, and is known to cause pneumonia, sepsis, rhinitis, endocarditis, and menigitis in pigs. The lectin responsible for *S. suis* adhesion has been identified (Pn and Po variants) and has been shown to bind to galabiose, binding to the Pk antigen, but not the P antigen (Haataja et al., J. Biol. Chem. 1993, 268:4311-17, herein incorporated by reference). As such, nanoparticles encapsulated in Pk antigen could be useful in treating *S. suis* infections.

i. Verotoxin Therapy

The present invention provides compositions for neutralizing verotoxin produced by *E. coli*. Subjects infected with verotoxin Producing Strains of *E. coli* may be treated by the carbohydrate encapsulated nano-particles of the present invention.

*E. coli* O157:H7 and other verotoxin-producing strains have gained widespread public attention in the United States due to their recently recognized association with two serious extraintestinal diseases, hemolytic uremic syndrome ("HUS") and thrombotic thrombocytopenic purpura ("TTP"). Worldwide, *E. coli* O157:H7 and other verotoxin-producing *E. coli* (VTEC) are an increasingly important human health problem. First identified as a cause of human illness in early 1982 following two outbreaks of food-related hemorrhagic colitis in Oregon and Michigan (M. A. Karmali, Clin. Microbiol. Rev., 2:15-38 [1989]; and L. W. Riley, et al., New Eng. J. Med., 308: 681-685 [1983]), the reported incidence of VTEC-associated disease has risen steadily, with outbreaks occurring in the U.S., Canada, and Europe.

With increased surveillance, *E. coli* O157:H7 has been recognized in other areas of the world including Mexico, China, Argentina, Belgium, and Thailand (N. V. Padhye and M. P. Doyle, J. Food. Prot., 55: 555-565 [1992]; and P. M. Griffin and R. V. Tauxe, Epidemiol. Rev., 13: 60 [1991]). The disease attracted national attention in the U.S. after a major outbreak in the Pacific Northwest that was associated with consumption of undercooked *E. coli* O157:H7-contaminated hamburgers. Over 700 hundred people fell ill (more than 170 were hospitalized) and four young children died. Several outbreaks since then have underscored the potential severity and multiple mechanisms for transmission of VTEC-associated diseases (M. Bielaszewska et al., Infection 18: 352-356 [1990]; A. Caprioli et al., J. Infect. Dis., 166: 184-158 [1992]; A. Caprioli, et al., J. Infect. Dis., 169: 208-211 [1994]; and N. Cimolai, Eur. J. Pediatr., 151: 147 [1992].

While O157:H7 is currently the predominant *E. coli* serotype associated with illness in North America, other serotypes (as shown in Table 1, and in particular O26:H11, O113:H121, O91:H21 and O111:NM) also produce verotoxins which appear to be important in the pathogenesis of gastrointestinal manifestations and the hemolytic uremic syndrome (M. M. Levine, et al., J. Clin. Microbiol., 30: 1636-1641 [1992]; and C. R. Dorn, et al., Epidemiol. Infect., 103: 83-95 [1989]). Since organisms with these serotypes have been shown to cause illness in humans they may assume greater public health importance over time.

Clinicians usually observe cases of hemolytic uremic syndrome ("HUS") clustered in a geographic region. However, small outbreaks are likely to be missed because many laboratories do not routinely screen stool specimens for *E. coli* O157:H7. Many cases related to non-commercial food preparation also probably go unrecognized. Nonetheless, *E. coli* O157:H7 is responsible for a large number of cases, as more than 20,000 cases of *E. coli* O157:H7 infection are reported annually in the U.S., with 400-500 deaths from HUS.

Risk factors for HUS progression following infection with *E. coli* O157:H7 include age (very young or elderly), bloody diarrhea, leukocytosis, fever, large amounts of ingested pathogen, previous gastrectomy, and the use of antimicrobial agents (in particular, trimethoprim-sulfamethoxazole) (M. A. Karmali, Clin. Microbiol. Rev., 2: 15-38 [1989]).

As indicated above, *E. coli* O157:H7 is associated with significant morbidity and mortality. The spectrum of illness associated with *E. coli* O157:H7 infection includes asymptomatic infection, mild uncomplicated diarrhea, hemorrhagic colitis, HUS, and TTP. Hemorrhagic colitis (or "ischemic colitis") is a distinct clinical syndrome characterized by sudden onset of abdominal cramps—likened to the pain associated with labor or appendicitis—followed within 24 hours by watery diarrhea. One to two days later, the diarrhea turns grossly bloody in approximately 90% of patients and has been described as "all blood and no stool" (C. H. Pai et al., Ann. Intern. Med., 101: 738-742 [1984]). Vomiting may occur, but there is little or no fever. The time from ingestion to first loose stool ranges from 3-9 days (with a mean of 4 days) L. W. Riley et al., New Eng. J. Med., 308: 681-685 [1983]; and D. Pudden et al., Ontario Can. Dis. Weekly Rpt., 11: 169-170 [1985]), and the duration of illness ranges generally from 2-9 days (with a mean of 4 days).

HUS is a life-threatening blood disorder that appears within 3-7 days following onset of diarrhea in 10-15% of patients. Those younger than 10 years and the elderly are at particular risk. Symptoms include renal glomerular damage, hemolytic anemia (rupturing of erythrocytes as they pass through damaged renal glomeruli), thrombocytopenia and acute kidney failure. Approximately 15% of patients with HUS die or suffer chronic renal failure. Indeed, HUS is a leading cause of renal failure in childhood.

TTP shares similar histopathologic findings with HUS, but usually results in multiorgan microvascular thrombosis. Neurological signs and fever are more prominent in TTP, compared with HUS. Generally occurring in adults, TTP is characterized by microangiopathic hemolytic anemia, profound thrombocytopenia, fluctuating neurologic signs, fever and mild azotemia (H. C. Kwaan, Semin. Hematol., 24: 71-81 [1987]; and S. J. Machin, Br. J. Hematol., 56: 191-197 [1984]). Patients often die from microthrombi in the brain. In one review of 271 cases, a rapidly progressive course was noted, with 75% of patients dying within 90 days (E. L. Amorosi and J. E. Ultmann, Med., 45:139-159 (1966). Other diseases associated with *E. coli* O157:H7 infection include hemorrhagic cystitis and balantitis.

Verotoxins are strongly linked to *E. coli* O157:H7 pathogenesis. All clinical isolates of *E. coli* O157:H7 have been shown to produce one or both verotoxins (VT1 and VT2). The VT1 and VT2 genes are carried by temperate coliphages 933J and 933W, respectively. Once lysogenized, these coliphages lead to the expression of toxin genes by the *E. coli* host.

Both of these toxins are cytotoxic to Vero (African green monkey kidney) and HeLa cells, and cause paralysis and death in mice. These toxins are sometimes referred to in the literature as Shiga-like toxins I and II (SLT-I and SLT-II, respectively), due to their similarities with the toxins produced by Shigella. Indeed, much of our understanding of *E. coli* VTs is based on information accumulated on Shiga toxins. Shiga toxin, first described in 1903, has been recognized as one of the most potent bacterial toxins for eukaryotic cells. Hereinafter, the VT convention will be used; thus, VT1 and VT2 correspond to SLT-I and SLT-II, respectively.

While the pathogenic mechanism of *E. coli* O157:H7 infection is incompletely understood, it is believed that ingested organisms adhere to and colonize the intestinal mucosa, where toxins are released which cause endothelial cell damage and bloody diarrhea. It is also postulated that hemorrhagic colitis progresses to HUS when verotoxins enter the bloodstream, damaging the endothelial cells of the microvasculature and triggering a cascade of events resulting in thrombus deposition in small vessels. These microthrombi occlude the microcapillaries of the kidneys (particularly in the glomeruli) and other organs, resulting in their failure. Verotoxins entering the bloodstream may also result in direct kidney cytotoxicity.

VT1 is immunologically and structurally indistinguishable from Shiga toxin produced by Shigella dysenteriae. VT1 and VT2 holotoxins each consist of one A and five B subunits (A. Donohue-Rolfe et al., Infect. Immun., 57: 3888-3893 [1989]; and A. Donohue-Rolfe et al., J. Exp. Med., 160: 1767-1781 [1984]). Intra-chain disulfide bonds are formed and the holotoxin is assembled after secretion of the subunits to the periplasm. Each subunit contains a leader sequence that targets secretion of the toxin. VT1 and VT2 are structurally related, sharing 56% amino acid homology.

The toxic A subunit is enzymatically active, while the B subunit binds the holotoxin to the receptor on the target eukaryotic cell. The A chain is structurally related to the ricin A chain, and acts in a similar manner to inhibit protein synthesis by cleaving a single adenine residue from 28S ribosomal RNA. The A chain is 32 (VT1) or 33 (VT2) kd in size, and is proteolytically cleaved into A1 (approximately 27 kd) and A2 (approximately 3-4 kd) fragments. In both VT1 and VT2, the non-toxic B subunit is approximately 8 kd. Pentamers of the B subunit bind mammalian cell surface receptors, facilitating internalization of holotoxin by cells.

Crystal structure analysis of Shiga holotoxin and VT1 B subunit pentamers have shown that the holotoxin assembles with the C-terminal end of the A subunit associating with, and inserting within, a pentamer of B chains. The alpha helical C-terminal region of the A chain (residues 279-293) is encircled by a pentameric ring of B subunits, with the remainder of the A chain exposed. This conformation is consistent with the observation that a C-terminally truncated A1 subunit of VT1 is toxic (in a ribosomal inhibition assay), but cannot associate with B subunit pentamers (P. R. Austin et al, Infect. Immun., 62: 1768 [1994]).

Various approaches to express recombinant verotoxins have included individual or coordinate expression of A and B subunits from high-copy number plasmids and expression with fusion partners (M. P. Jackson et al., J. Bacteriol., 172: 3346-3350 [1990]; M. P. Jackson et al., FEMS Microbiol. Lett., 44: 109-114 [1987]; F. Gunzer and H. Karch, J. Clin. Microbiol., 31: 2604-2610 [1993]; and D. W. Acheson et al., Infect. Immun., 63:301-308 [1995]).

The receptor for VT1 and VT2 is globotriaosyl ceramide (Pk antigen or Gb3 or CD77) containing a terminal galabiosyl disaccharide (Galα 1-4Gal) (C. A. Lingwood et al., J. Biol. Chem., 262: 1779-1785 [1987]; and T. Wadell et al., Biochem. Biophys. Res. Commun., 152: 674-679 [1987]). Pk antigen is abundant in the cortex of the human kidney and is present in primary human endothelial cell cultures. Hence, the identification of Pk antigen as the functional receptor for VT1 and VT2 is consistent with their role in HUS pathogenesis, in which endothelial cells of the renal vasculature are the principal site of damage. Therefore, toxin-mediated pathogenesis may follow a sequence of B subunit binding to Pk antigen receptors on kidney cells, toxin internalization, enzymatic reduction of the A subunit to an A1 fragment, binding of the A1 subunit to the 60S ribosomal subunit, inhibition of protein synthesis and cell death.

In some embodiments, pK antigen (or an analog thereof) encapsulted nanoparticle (e.g. nanoparticle) is used to treat verotoxin producing E. coli in a subject. All of the disease and E. coli serotypes discussed above may be treated. In some embodiments, hemolytic uremic syndrome ("HUS") is treated, while in other embodiments thrombotic thrombocytopenic purpura ("TTP") is treated.

The present invention also provides compositions for delivering carbohydrate therapeutics in a multivalent fashion that are known or that are discovered through the new efforts in glycomics. The compositions of the present invention will allow this new class of therapeutics (i.e. carbohydrates) to be delivered in a safe and efficacious manner.

C. Therapeutic Formulations and Modes of Delivery

Depending on the condition being treated (see above), compositions comprising carbohydrate encapsulated nanoparticles may be formulated and administered systemically or locally. Techniques for formulation and administration may be found in the latest edition of "Remington's Pharmaceutical Sciences" (Mack Publishing Co, Easton, Pa.).

The invention contemplates administering therapeutic compounds in accordance with acceptable pharmaceutical delivery methods and preparation techniques. For example, some therapeutic compounds of the present invention are administered to a subject intravenously in a pharmaceutically acceptable carrier such as physiological saline. For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Standard methods for intracellular delivery of pharmaceutical agents are used in other embodiments (e.g., delivery via liposome). Such methods are well known to those of ordinary skill in the art.

In some other embodiments, therapeutic agents are formulated for parenteral administration, such as, intravenous, subcutaneous, intramuscular, intraperitoneal and the like. In some embodiments, the therapeutic agents in for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Therapeutic co-administration of some contemplated anti-cancer agents (e.g., therapeutic polypeptides) can also be accomplished using gene therapy described herein and commonly known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, dragees, liquids, gels, syrups, slurries, suspensions and the like, for oral or nasal ingestion by a patient to be treated. In some preferred embodiments, the therapeutic compounds are administered orally to a patient orally.

Pharmaceutical preparations for oral use can be obtained by combining the active compounds (e.g., encapsulated nanoparticles) with a solid excipient, optionally grinding the resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc.; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Ingestible formulations of the present compositions may further include any material approved by the United States Department of Agriculture for inclusion in foodstuffs and substances that are generally recognized as safe (GRAS), such as, food additives, flavorings, colorings, vitamins, minerals, and phytonutrients. The term phytonutrients as used herein, refers to organic compounds isolated from plants that have a biological effect, and includes, but is not limited to, compounds of the following classes: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

In some embodiments of the present invention, therapeutic agents are administered to a patient alone, or in combination with one or more other drugs or therapies (e.g., conventional anticancer agents, including, but not limited to, nucleotide sequences, drugs, hormones, etc.) or in pharmaceutical compositions where it is mixed with excipient(s) or other pharmaceutically acceptable carriers. In one embodiment of the present invention, the pharmaceutically acceptable carrier is pharmaceutically inert.

Pharmaceutical compositions suitable for use in the present invention include compositions wherein the active ingredients are contained in an effective amount to achieve the intended purpose. For example, an effective amount of therapeutic compound(s) may be that amount that inhibits hyperproliferation, angiogenesis, cell migration, cell adhesion, and/or cell survival in a cell as compared to control cells.

In addition to the active ingredients, preferred pharmaceutical compositions optionally comprise pharmaceutically acceptable carriers, such as, excipients and auxiliaries that facilitate processing of the active compounds into preparations which can be used pharmaceutically.

In some embodiments, the pharmaceutical compositions used in the methods of the present invention are manufactured according to well known and standard pharmaceutical manufacturing techniques (e.g., by means of conventional mixing, dissolving, granulating, dragee-making, levigating, emulsifying, encapsulating, entrapping or lyophilizing processes).

Compositions comprising a compound of the invention formulated in a pharmaceutical acceptable carrier may be prepared, placed in an appropriate container, and labeled for treatment of an indicated condition. In some embodiments, the pharmaceutical compositions are provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual therapeutic agents, and can generally be estimated based on $EC_{50}$s found to be effective in in vitro and in vivo animal models or based on the examples described herein. Additional factors which may be taken into account include the severity of the disease state; age, weight, and gender of the patient; diet, time and frequency of administration, drug combination(s), reaction sensitivities, and tolerance/response to therapy. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the therapeutic agent is administered in maintenance doses, ranging from 0.01 μg to 100 g per kg of body weight, once or more daily, to once about every 20 years.

For any compound used in the methods of the invention, the therapeutically effective dose can be estimated initially from cell culture assays. Then, preferably, dosage can be formulated in animal models (particularly murine or rat models) to achieve a desirable circulating concentration range that results in increased PKA activity in cells/tissues characterized by undesirable cell migration, angiogenesis, cell migration, cell adhesion, and/or cell survival. A therapeutically effective dose refers to that amount of therapeutic compound(s) that ameliorate symptoms of the disease state (e.g., hyperproliferation, unregulated angiogenesis, cell migration, and/or loss of apoptotic control). Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from cell culture assays and additional animal studies can be used in formulating a range of dosage, for example, mammalian use (e.g., humans). The dosage of such compounds lies preferably, however the present invention is not limited to this range, within a range of circulating concentrations that include the $ED_{50}$ with little or no toxicity.

Guidance as to particular dosages and methods of delivery is provided in the literature (See, U.S. Pat. Nos. 4,657,760; 5,206,344; or 5,225,212, all of which are herein incorporated by reference in their entireties). Administration of some agents to a patient's bone marrow may necessitate delivery in a manner different from intravenous injections.

III. Screening Assays, Arrays and Imaging

In some embodiments, the carbohydrate encapsulated nanoparticles of the present invention are used in screening assay or as part of arrays to detect target compounds (e.g. FimH, PapG, verotoxin, etc.) in sample. In other embodiments, the target molecule is a drug candidate. In certain embodiments, the carbohydrate nanoparticles are employed in vivo diagnostics such that certain target molecules can be imaged in vivo (e.g. to check the type of bacteria or cancer in a subject, and to determine what quantity is present).

In some embodiments, the nanoparticles of the present invention are immobilized (e.g. in an array) by depositing them in a substantially uniformly layer on a support. Methods of immobilizing nano- and/or ultrafine gold particles on supports are described in U.S. Pat. Nos. 4,698,324; 4,839,327; 4,937,219; 5,051,394; 5,506,273 (each of which is incorporated herein by reference in its entirety).

Certain embodiments of the presently claimed invention contemplate the generation of a large palette (array) of encapsulated nanoparticles with various ligand/receptor capabilities within a single device (e.g., covalently attached to a substrate and/or bound in permeable matrix, such as a sol-gel) to increase selectivity, sensitivity, quantitation, ease of use, portability, among other desired characteristics and qualities. By using the array format, several advantages can be realized that overcome the shortcomings of existing analytes sensors. These include the ability to use partially selective sensors and to measure multicomponent samples. This offers the possibility of sensing a specific analyte in the presence of an interfering background, or to monitor two or more analytes of interest at the same time. The higher the number of elements (e.g., encapsulated nanoparticles) in an array, the greater the chance of a positive identification of a given analyte. By immobilizing the nanoparticles, assay materials of any desired size and shape can be created and incorporated into convenient and easily read assay devices The nanoparticles of the present invention are preferably employed for detecting the presence or absence of target molecules (e.g. target molecules in a test sample). Any method for detecting target molecules may be performed with the carbohydrate encapsulated nanoparticles of the present invention (e.g. simple binding assays, or more complex assays with multiple components). In some embodiments, one component of a detection assay is the nanoparticles of the present invention and other components of a detection assay (e.g., secondary antibody, etc.) may then be added before, after, or simultaneously with a sample suspected of containing target molecules (i.e. a test sample). In certain embodiments, the test sample is contacted with the nanoparticles of the present invention and various operations are carried out, such as the addition of miscellaneous reagents, incubations, washings, and the like. In this regard, substrates coated with the nanoparticles of the present invention may carry out thousands of detection reactions to determine if target molecules are present in a test sample. In certain embodiments, the target molecules are pathogenic *E. coli* bacteria, verotoxin, *S. suis*, type 1 pili, FimH, or PapG.

In some embodiments, the nanoparticles of the present invention are employed with immunoassay procedures. Any type of immunoassay may be employed with the nanoparticles of the present invention (see, e.g., U.S. Pat. Nos. 4,016,043; 4,424,279 and 4,018,653, all of which are herein incorporated by reference). For example, a one-step sandwich immunoassay may be performed by first mixing a secondary labeled antibody with a test sample and incubating, flowing this mixture over an array of the nanoparticles of the present invention, and then incubating. Finally, the array of nanoparticles are washed, and bound targets are detected. This procedure may also be employed in a competitive binding assay format where the secondary labeled antibody would compete for the nanoparticle instead of binding to the target. Another example is a two-step sandwich immunoassay that may be employed by flowing a test sample over an array of immobilized nanoparticles and then incubated. Next, the immobilized nanoparticles in the array are washed. Then a secondary labeled antibody reagent is applied to the surface of the array, and the array is washed. This procedure may also be employed, for example, for a delayed-addition competitive binding assay where the labeled antibody reagent would bind to unoccupied sites on the nanoparticles.

The present invention may be employed to detect any type of target molecule in a test sample, including candidate carbohydrate drugs molecules. Further examples of targets that may be detected by the nanoparticles of the present invention are viruses, prokaryotic and eukaryotic cells, unicellular and polycellular organism cells, e.g., fungi, animal, mammal, etc., or fragments thereof. The microarrays (composed of carbohydrate encapsulated nanoparticles immobilized on a substrate) of the present invention may be used for detecting pathogens. For example, mannose (or derivatives thereof), the Pk antigen (or analogs thereof), or other pathogen specific carbohydrates may be used in any type of detection assay to detect pathogens. Pathogens of interest may be viruses such as Herpesviruses, Poxviruses, Togaviruses, Flaviviruses, Picornaviruses, Orthomyxoviruses, Paramyxoviruses, Rhabdoviruses, Coronaviruses, Arenaviruses, and Retroviruses. Targets may also include bacteria including, but not limited to, *Escherichia coli*, *Pseudomonas aeruginosa*, *Enterobacter cloacae*, *Staphylococcus aureus*, *Enterococcus faecalis*, *Klebsiella pneumoniae*, *Salmonella typhimurium*, *Staphylococcus epidermidis*, *Serratia marcescens*, *Mycobacterium bovis*, methicillin resistant *Staphylococcus aureus* and *Proteus vulgaris*. The examples of such pathogens are not limited to above pathogens. A non-exhaustive list of these organisms and associated diseases can be found for example in U.S. Pat. No. 5,795,158 issued to Warinner and incorporated herein by reference.

Assays using the nanoparticles of the present invention can be carried out with a test sample (e.g. biological fluid), including, but not limited to, separated or unfiltered biological fluids such as urine, cerebrospinal fluid, pleural fluid, synovial fluid, peritoneal fluid, amniotic fluid, gastric fluid, blood, serum, plasma, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which may contain the target of interest. Other similar specimens such as cell or tissue culture or culture broth may also be employed. Alternatively, the test sample may be obtained from an environmental source such as soil, water, or air; or from an industrial source such as taken from a waste stream, a water source, a supply line, or a production lot. Industrial sources also include fermentation media, such as from a biological reactor or food fermentation process such as brewing; or foodstuff, such as meat, game, produce, or dairy products. The test sample can be pre-treated prior to use, such as preparing plasma from blood, diluting viscous fluids, or the like; methods of treatment can involve filtration, distillation, concentration, inactivation of interfering compounds, and the addition of reagents.

The carbohydrate encapsulated nanoparticles of the present invention (e.g. immobilized on a substrate in an array) may also be used to assay test compounds, for example, to evaluate their potential as a therapeutic. For example, the ability of test compounds to serve as agonists or antagonists in certain binding reactions (e.g. where the binding partners are known, and one of them is attached to the nanoparticles) may be evaluated.

In some preferred embodiments, the nanoparticles of the present invention are encapsulated in mannose or a mannose derivative, and an assay is run with FimH and a test compound suspected of interfering with mannose-FimH binding. In other embodiments, a screening assay is run with Pk antigen encapsulated nanoparticles, verotoxin, and a test compound suspected of disrupting the binding between the Pk antigen and verotoxin (e.g. to find compounds that might be used to treat verotoxin in toxication).

A. Detecting Targets

In certain embodiments of the present invention, after an assay has been performed, the nanoparticles are read to determine the identity of the nanoparticles generating a signal (or to ascertain geometric properties of particles such as shape or size), and in some embodiments where a label is used, the amount of label bound. Any method may be employed to detect a signal that is generated. Examples of means that may be used for detection and analysis include, but are not limited to, visual inspection, electron microscope, optical microscope, optical spectroscopy, digital (CCD) cameras, video cameras, photographic film, or the use of current instrumentation such as laser scanning devices, fluorometers, luminometers, photodiodes, quantum counters, plate readers, epifluorescence microscopes, scanning microscopes, confocal microscopes, capillary electrophoresis detectors, or by other means for amplifying the signal such as a photomultiplier tube or other light detector capable of detecting the presence, location, intensity, excitation and emission spectra, fluorescence polarization, fluorescence lifetime, and other physical properties of the fluorescent signal.

In certain preferred embodiments, gold nanoparticles of different shapers are employed. Spherical gold nanoparticles tend to be red, while rod-shaped nanoparticles tend to be blue or purple. As such, using different shapes allows multiple targets to be assayed at once.

In certain embodiments, the carbohydrate encapsulated nanoparticles are employed in vivo to provide an image of a certain target (e.g. cancer cells, pathogens, etc.). In some embodiments, the nanoparticles incorporate fluorescent or radioactive molecules for this purpose. In other embodiments, the carbohydrate encapsulated nanoparticles of the present invention are used to label proteins on cells surfaces, which can the be viewed (e.g. by TEM).

EXPERIMENTAL

The following examples are provided in order to demonstrate and further illustrate certain preferred embodiments and- aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); DS (dextran sulfate); and C (degrees Centigrade).

Example 1

1-Bromo 2,3,4,6-tetra-O-acetyl-mannopyranoside (Compound 2)

2,3,4,5,6-Penta-O-acetyl-mannopyranoside (10.0 g, 25.6 mmol) was treated with HBr in AcOH (15 mL of a 33% solution) at 25° C. After stirring for 90 min, the solution was diluted with $CHCl_3$ (100 mL) and then extracted with ice-cold $H_2O$ (200 mL×3). The organic layer was neutralized by $Na_2CO_3$, and washed with brine, dried over $Na_2SO_4$, and finally concentrated. The desired bromide (compound 2) was used for next step without further purification.

Example 2

Pent-4-enyl 2,3,4,6-tetra-O-acetyl-B-D-mannopyranoside (Compound 3)

The syrup of compound 2 was co-evaporated with toluene twice before use. To a solution of compound 2 (10.0 g, 42 mmol) in toluene-acetonitrile solution (100 ml, v/v=1:1) was added derierite (5 g), 4-pentene-1-ol (4.6 mL, 59 mmol) and mercury(II) cyanide (12.0 g, 47.5 mmol). The mixture was stirred overnight at room temperature and then filtered. The resulting residue was dissolved in chloroform (100 mL) and washed with $NaCl_{(sat)}$. The organic layer was dried over $Na_2SO_4$, filtered and concentrated. The residue was purified by a flash column chromatography (EtOAc/hexane=1/1) to give compound 3 (8.4 g) in 88% yield. $^1H$ NMR (400 MHz, $CDCl_3$) δ 1.69-1.76 (m, 2H), 2.00 (s, 3H), 2.05 (s, 3H), 2.09-2.21 (m, 2H), 2.10 (s, 3H), 2.16 (s, 3H), 3.47 (dt, J=13.2, 6.4 Hz, 1H), 3.70 (dt, J=13.2, 6.4 Hz, 1H), 3.99 (ddd, J=10.0, 5.2, 2.8 Hz, 1H), 4.1 1(dd, J=12.0, 2.8 Hz, 1H), 4.27 (dd, J=12.0, 5.2 Hz, 1H), 4.80 (d, J=1.6 Hz, 1H), 4.98-5.08 (m, 2H), 5.23-5.30 (m, 2H), 5.35 (dd, J=10.0, 3.6 Hz, 1H), 5.76-5.86 (m, 1H); $^{13}C$ NMR (100 MHz, $CDCl_3$) b 20.37×2, 20.72×2, 28.57, 30.30, 61.83, 66.79, 68.35, 71.03, 71.89, 72.73, 100.80, 115.41, 138.27, 169.64, 169.94×3.

Example 3

5-Thioacetoxypentyl 2,3,4,6-tetra-O-acetyl-α-D-mannopyranosyl Dimer (Compound 4)

A solution of compound 3 (500 mg, 1.15 mmol), thioacetic acid (0.5 mL, 0.85 mmol), and AIBN (95 mg, 0.1 mmol) in 1,4-dioxane (20 mL) was thoroughly degassed ($N_2$) before being reacted at 75° C. After stirring for 6 h, the reaction was quenched with cyclohexene (3 mL), concentrated and co-concentrated twice with toluene. The residue was then subjected to flash chromatography (EtOAc/hexane=1/1) to yield sulfide spacer derivative (460 mg, in 80% yield). $^1H$ NMR (400 MHz, $CDCl_3$) δ 1.42-1.48 (m, 2H), 1.58-1.66 (m, 4H), 2.00 (s, 3H), 2.05 (s, 3H), 2.11 (s, 3H), 2.16 3H), 2.34 (s, 3H), 2.89 (t, J=7.2 Hz, 2H), 3.45 (dt, J=12.8, 6.4 Hz, 1H), 3.69 (m, J=13.2, 6.4 Hz, 1H), 3.96-4.00 (m, 1H), 4.11(dd, J=12.4, 2.4 Hz, 1H), 4.29 (dd, J=12.4, 5.2 Hz, 1H), 4.80 (d, J=1.6 Hz, 1H), 5.23-5.31 (m, 2H), 5.33 (dd, J=10.0, 6.8 Hz, 1H); $^{13}C$ NMR (100 MHz, CDCl$_3$) δ20.36×2, 20.73×2, 24.37, 28.28, 28.81, 28.98, 30.76, 61.82, 68.23, 68.36, 71.02, 71.88, 72.72, 100.81, 169.64×4, 194.84. The above compound (700 mg, 0.98 mmol) in methanol (5 mL) was treated with sodium methoxide (10 mg) and stirred at room temperature for 0.5 h. After concentration, the resulting residue was dissolved in water (3 mL) and then passed through a Biogel P2 column to yield the pure compound 4 (380 mg, 97% yield) as a white lyophilisate. $^1$H NMR (400 MHz, CD$_3$OD) δ 1.49-1.56 (m, 2H), 1.61-1.67 (m, 2H), 1.71-1.78 (m, 2H), 2.72 (t, J=7.3 Hz, 2H), 3.43-3.47 (m, 1H), 3.52-3.57 (m, 1H), 3.63 (t, J=9.6 Hz, 1H), 3.70-3.78 (m, 3H), 3.81 (dd, J=3.3, 1.7 Hz, 1H), 3.84 (dd, J=1 1.7, 2.4 Hz, 1H), 4.76 (d, J=1.6 Hz, 1H); $^{13}$C NMR (100 MHz, CD$_3$OD) 24.28, 24.39, 28.81, 33.62, 62.49, 68.37, 70.30, 72.27, 74.78, 76.75, 106.89.

Example 4

Synthesis and Characterization of Mannose Encapsulated Gold Nanoparticles (m-AuNP) (Compound 1)

An aqueous solution of HAuCl$_4$ (3 mL, 15 mmol L−1) was added to a toluene solution (3 mL, 35 mmol L$^{-1}$) in the presence of tetraoctylammonium bromide (2 mg) at room temperature. After stirring for 1 min, the organic layer was separated. Sodium borohydride (3 mg) was slowly added to a freshly prepared methanol solution of compound 4 (5 mg) with vigorous stirring. After stirring for 0.5 h, gold nanoparticles were precipitated by centrifugation and then washed with methanol (20 mL×3). The mannose encapsulated nanoparticle were dried under vacuum for overnight.

The $^1$H NMR spectrum (400 MHz, D$_2$O) of m-AuNP showed that two broadened peaks appeared in the ranges of 1.12-2.20 ppm and 3.40-4.00 ppm, separately. The chemical shifts of the peaks correspond to those of compound 4. Previous reports have indicated that the broadened peaks may be attributed to the assembly of thiolated mannose on gold surface (Hostetler, M. J. et al *Langmuir* 1998, 14, 17).

The spherical mannose m-AuNP, with an average diameter of 6±1 nm were observed by TEM, and no aggregation was found in the images. Both UV-visible spectra of gold nanoparticles before and after coupling with mannose showed clear plasmon bands of 7-520 nm. No red-shift or intensity decrease of the bands after modification also indicated that no aggregation occurred in aqueous media. The X-ray photoelectron spectrum (XPS) of m-AuNP solid was different from that of unbound thiols (S—H). Particularly, a large binding energy difference was observed fro S2P$_{3/2}$ (~1.8 eV). This result indicates that a thiolate (S—Au) is indeed present in m-AuNP. In addition, the formation of m-AuNP was also confirmed by the transmission IR and NMR spectra. Furthermore, it was estimated that a single m-AuNP contains approximately 200 mannoses, as estimated from the average nanoparticle diameter and result of elemental analysis.

UV-vis Absorption Spectroscopy

Figure 3:
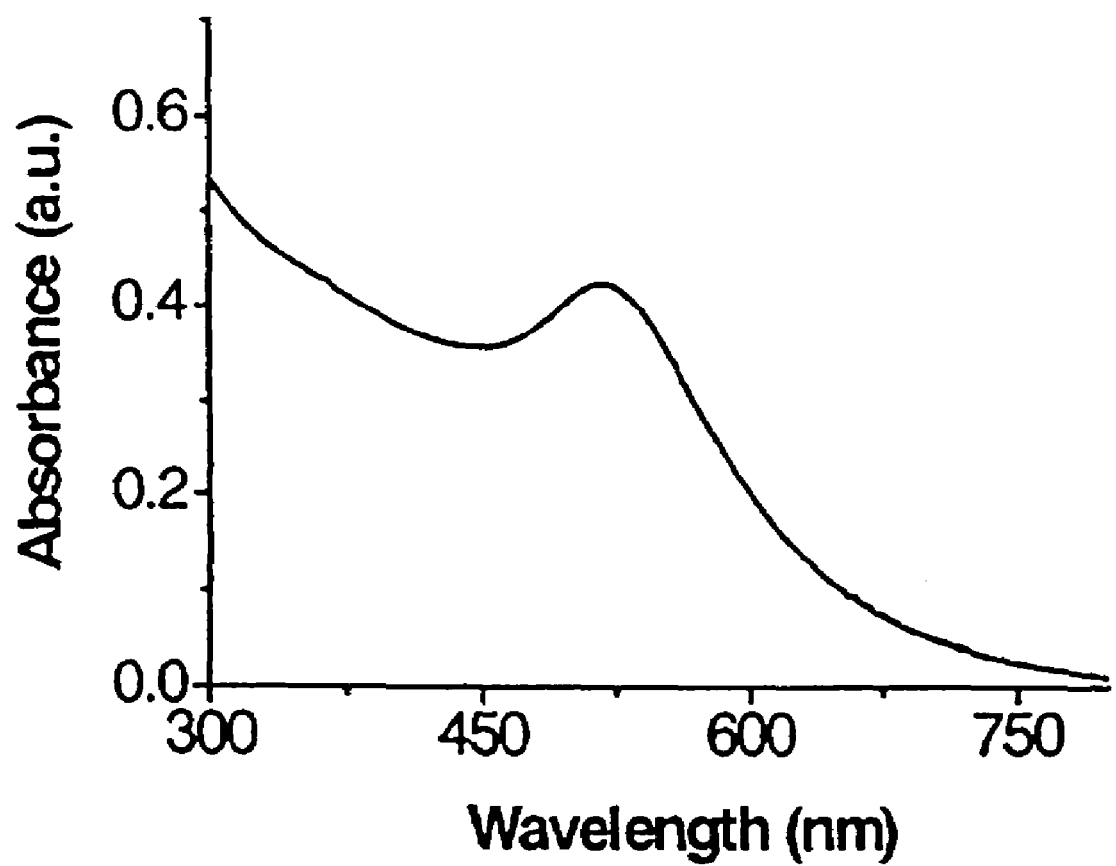
FIG. 3 shows UV-vis absorption spectroscopy results generated in Example 4.

A typical m-AuNP solution for the stability study was prepared by dissolving 3 mg m-AuNP in 10 ml, water (O.D value 0.504). The above solution was mixed with different media in v/v=1/1 ratio. The measurements were recorded on UV-near-IR spectrometers (Perkin Elmer, λ-900 and HP-8453). FIG. 3 shows a typical UV-visible spectrum of mannose encapsulated nanoparticles.

X-ray Photoelectron Spectroscopy

Figure 4:
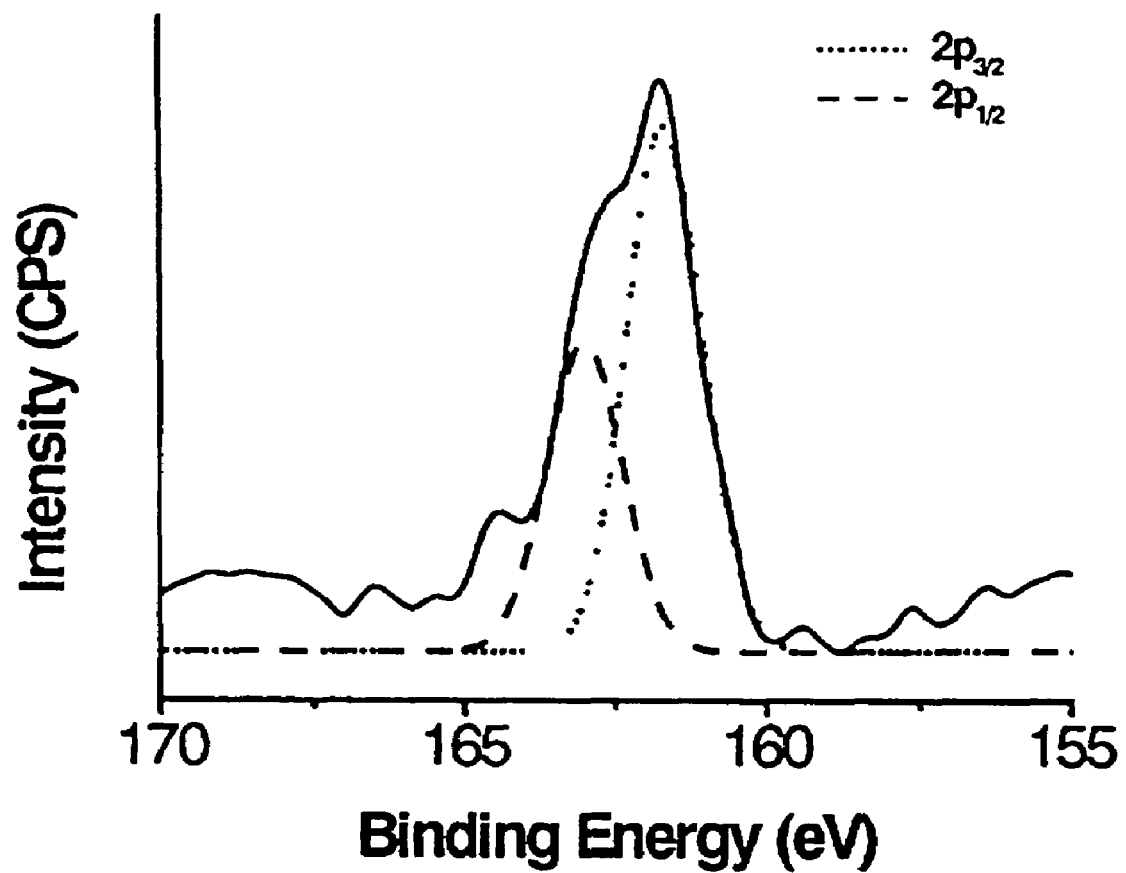
FIG. 4 shows certain X-ray photoelectron spectroscopy results generated in Example 4.

The sample was prepared by the direct deposition of m-AuNP solid onto a double sided conductive copper tape (4×4 mm$^2$). The XPS measurement was carried on the Omicron system attached with a hemispherical analyzer (EAC 2000-125) and with an Al Kα source (hv=1486.6 eV). FIG. 4 shows an X-ray photoelectron spectrum (solid line) of m-AuNP solid. All S 2p spectra exhibited only S 2p doublet with binding energy of −163.0 eV (S 2p$_{1/2}$) and 161.7 eV (S 2p$_{3/2}$) determined from the fit (dotted lines) of the data. The large binding energy difference (−1.8 eV) with respect to unbound thiols (S—H, 163.5 eV for S 2p$_{3/2}$) suggests that the single species is indeed a thiolate (Au—S).

Transmission IR Spectroscopy

Figure 5:
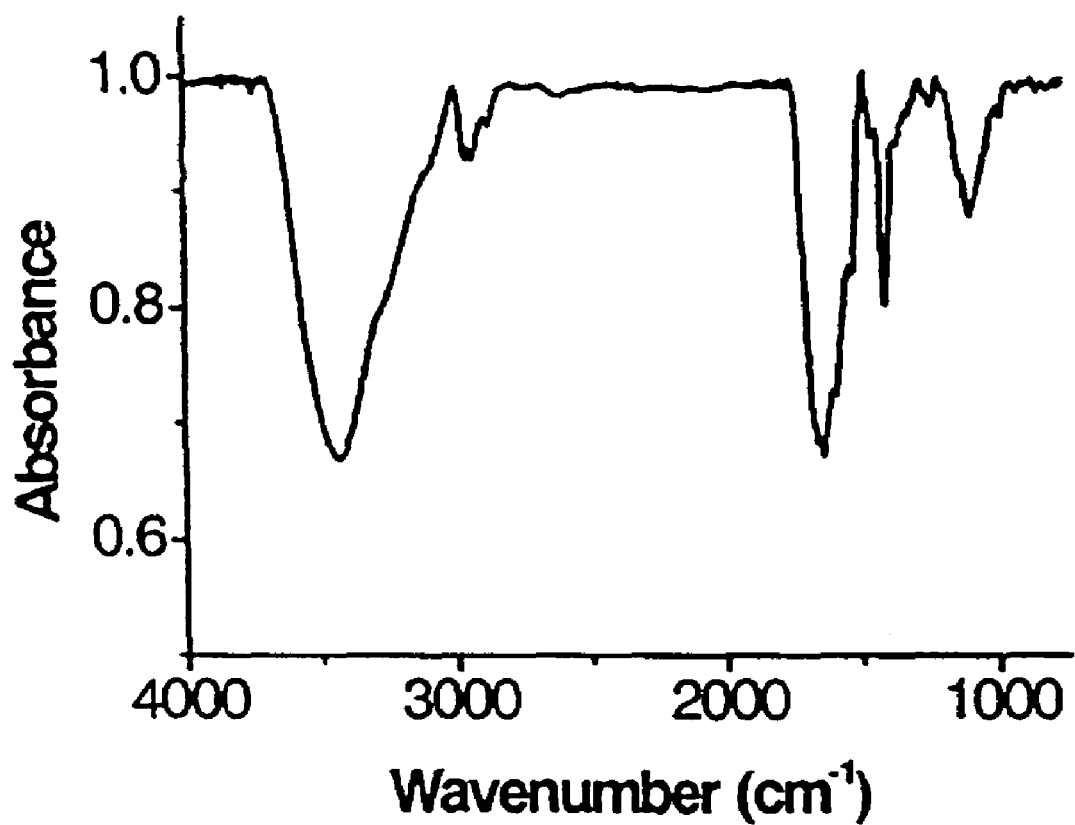
FIG. 5 shows certain transmission IR spectroscopy results generated in Example 4.

The spectra were obtained from a pelleted sample made of the mixture of m-AuNP (5 mg) and KBr (10 mg). The measurements were performed on a Perkin Elmer 682 spectrometer. FIG. 5 shows a typical UV-visible spectrum of mannose encapsulated nanoparticles. Transmission IR spectrum of m-AuNP. The absence of S—H stretch band between 2650 and 2450 cm$^{-1}$ suggested that gold-sulfur bond was formed in the reaction.

Example 5

Gold Nanoparticle Dispersion Stability

Figure 6:
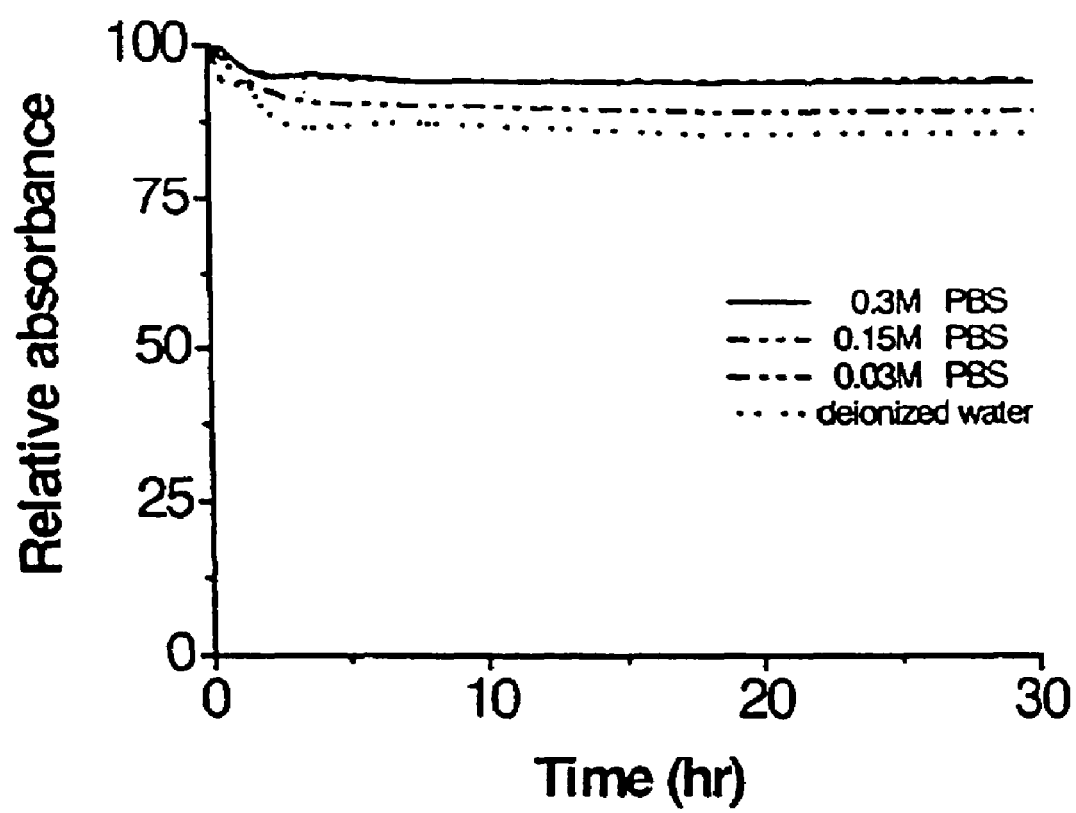
FIG. 6 shows certain dispersion stability results generated in Example 5.

Experiments were conducted to determine the dispersion stability of m-AuNP in different concentrations of PBS buffers versus time. The stability is judged by the relative intensity of surface plasmon band (520 nm) of m-AuNP changes with time. Similar plots (not shown) were also obtained when the solutions with high ion strength solutions (Na+ and W), and with different pH values (1.5 to 12) were applied. FIG. 6 shows the results of these experiments. The results of this experiment show that the mannose encapsulated nanoparticles were found to be very stable in deionized water and phosphate buffered solution (PBS), and its stability was independent of high ion strength and pH values in the range from 1.5 to 12 of solutions, as suggested by the absorption spectra. Moreover, the mannose encapsulated gold nanoparticles were found to be easily redissolved in aqueous media without aggregation.

Example 6

Binding of m-AuNP to *E. coli* Type 1 Pili

The ability of m-AuNP to bind mannose-specific adhesin Fimr of type I pili in *E. coli* was then tested. Two *E. coli* strains, ORN 178 and ORN 208 were used in this example to confirm the specific binding of m-AuNP to FimH. The ORN 178 strain expresses the wild-type 1 pili, whereas the ORN 208 strain is deficient of the fimH gene and expresses abnormal type I pili that fail to mediate D-mannose specific binding. The *E. coli* K-12 strains ORN178 and ORN208 were grown in LB medium at 37° C. to an optical density of 0.7 at 600 nm (approximately 10$^9$ cells per mL). Bacteria from 200 μL culture was precipitated by centrifugation at 3,000 g for 5 min, redissolved in 200 μL binding buffer (LB, phosphate buffered saline or water) and followed by adding 10 μL nanoparticle solution. The resulting bacteria and nanoparticle mixtures were incubated at various temperatures (4, 25, or 37° C.) with mild shaking for 30 min. After washing three times with binding buffer, bacteria were redissolved in 10-20 µL binding buffer.

Figure 2A:
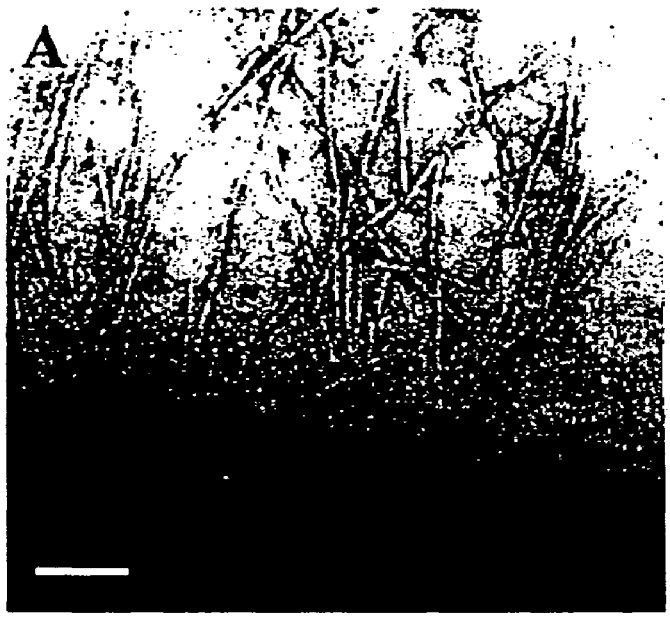
FIG. 2 shows TEM images of wild-type E. coli type 1 pili bound by m-AuNP (2A) and E. coli pili deficient in FimH without m-AuNP (2B). Scale bar in this figures equal 100 nm.
Figure 2B:
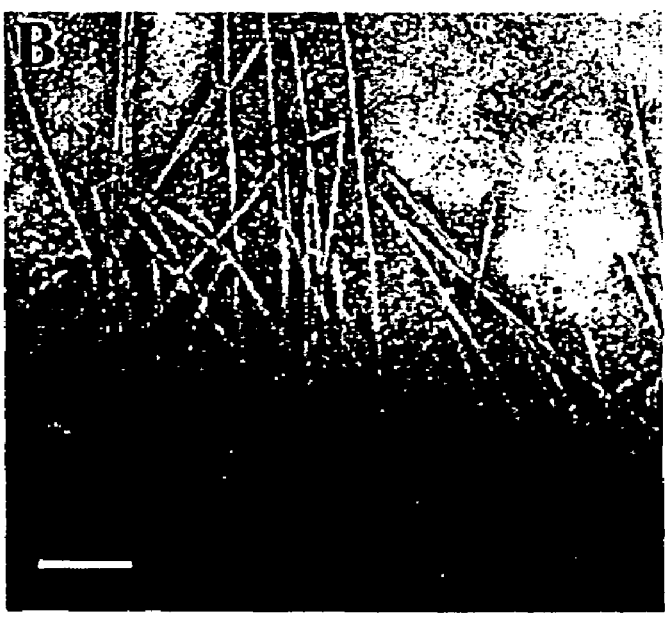

The binding of m-AuNP to bacterial pili in each condition were examined by TEM. The TEM results showed that m-AuNP selectively bound the pili of the ORN178 strain but not those of the ORN208 strain (See FIG. 2), demonstrating specific binding of m-AuNP to FimH. The selective binding of the ORN178 was observed in all buffers and temperatures tested. However, the best result was obtained at 25 degrees Celsius. The nanoparticles were localized at the lateral ends and distributed at intervals along the shaft of the pili (on the average of 100-150 nm interval) in ORN178 strain, consistent with the localization pattern of FimH protein along type 1 pili viewed by electron microscopy.

Example 7

Competition Binding Assay of m-AuNP and Free Mannose for Bacterial Type 1 Pili

This example was performed to test the binding of ability of m-AuNP with respect to free mannose in solution. Specifically, methyl a-D-mannopyranoside was used as competitor of m-AuNP for FimH in binding experiments. Mannose at various concentrations (see Table 2) and m-AuNP were co-incubated with ORN178 to reach an equilibrium, and the binding of m-AuNP to bacterial pili was examined by TEM. Free mannose at concentrations up to twenty times of m-AuNP concentration had no or little effect on the binding of m-AuNP to bacterial pili. Mannose concentrations required for competing out ~10 and ~90% of m-AuNP binding to bacterial pili were approximately 100 and 2000 times of m-AuNP. These results indicate that m-AuNP binds FimH better than free mannose.

TABLE 2

Competition binding assay of m-AuNP and mannose to type 1 pili in *E. coli*

| m-AuNP:mannose[1] | Percentage of m-AuNP binding to pili[2] |
|---|---|
| 1:1 | ~100% |
| 1:10 | ~100% |
| 1:20 | >90% |
| 1:100 | >50% |
| 1:200 | <50% |
| 1:2000 | <10% |
| 1:20000 | 0% |

[1]Concentration ratio of m-AuNP and methyl α-D-mannopyranoside.
[2]The percentages were calculated from the ratios of the numbers of m-AuNP binding to pili in the presence of various mannose concentrations relative to the number of m-AuNP binding to pili without free mannose. The number of m-AuNP binding to pili was obtained by counting the nanoparticles on ~100 pili in TEM images.

Example 8

Generating pK Antigen (Glabotriose) Encapsulated Gold Particles

Figure 8:
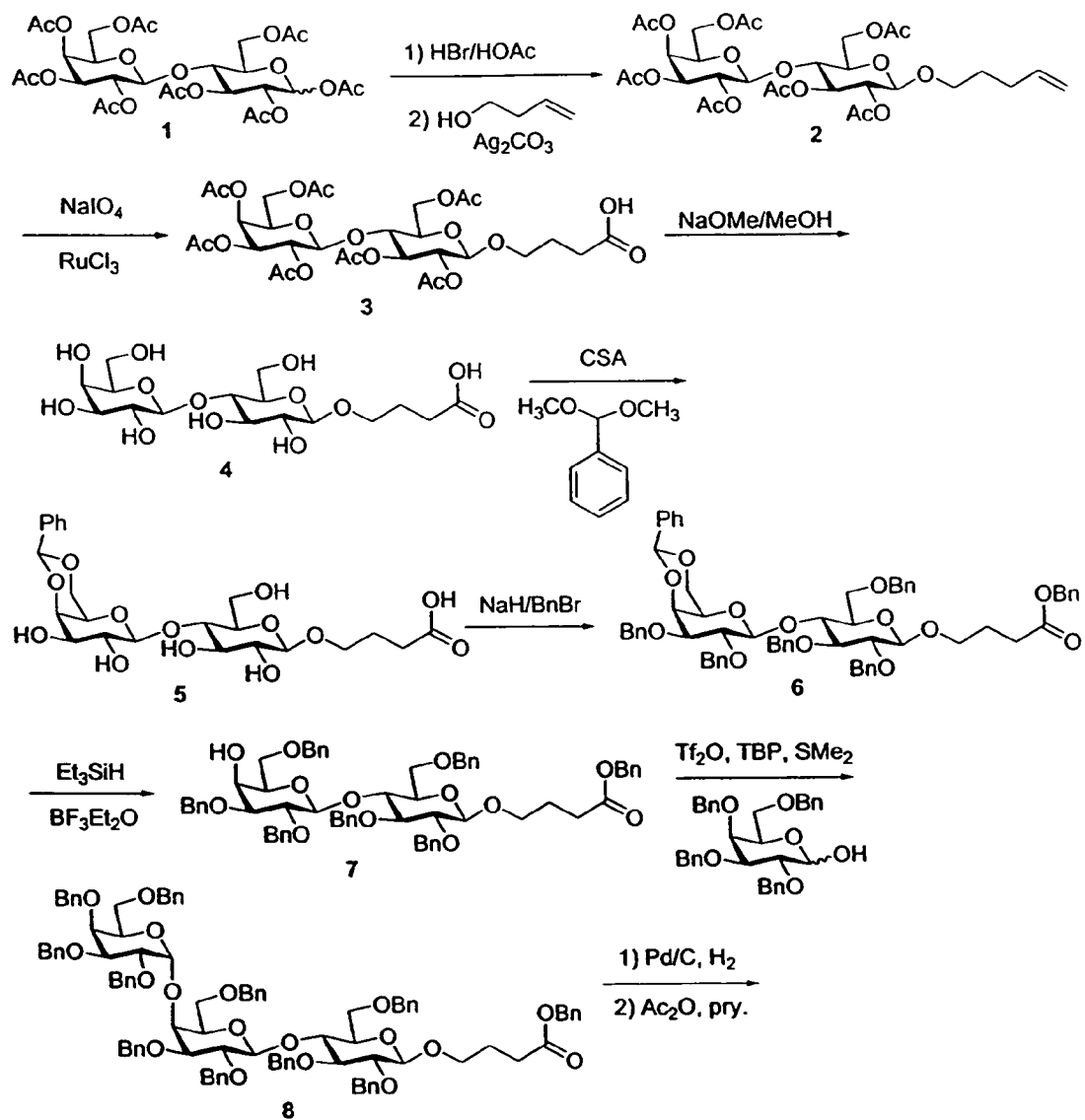
FIG. 8 shows steps that may be taken to synthesize thiolated pK antigen (which may be attached to gold particles, for example, as described in Example 4).
Figure 8:
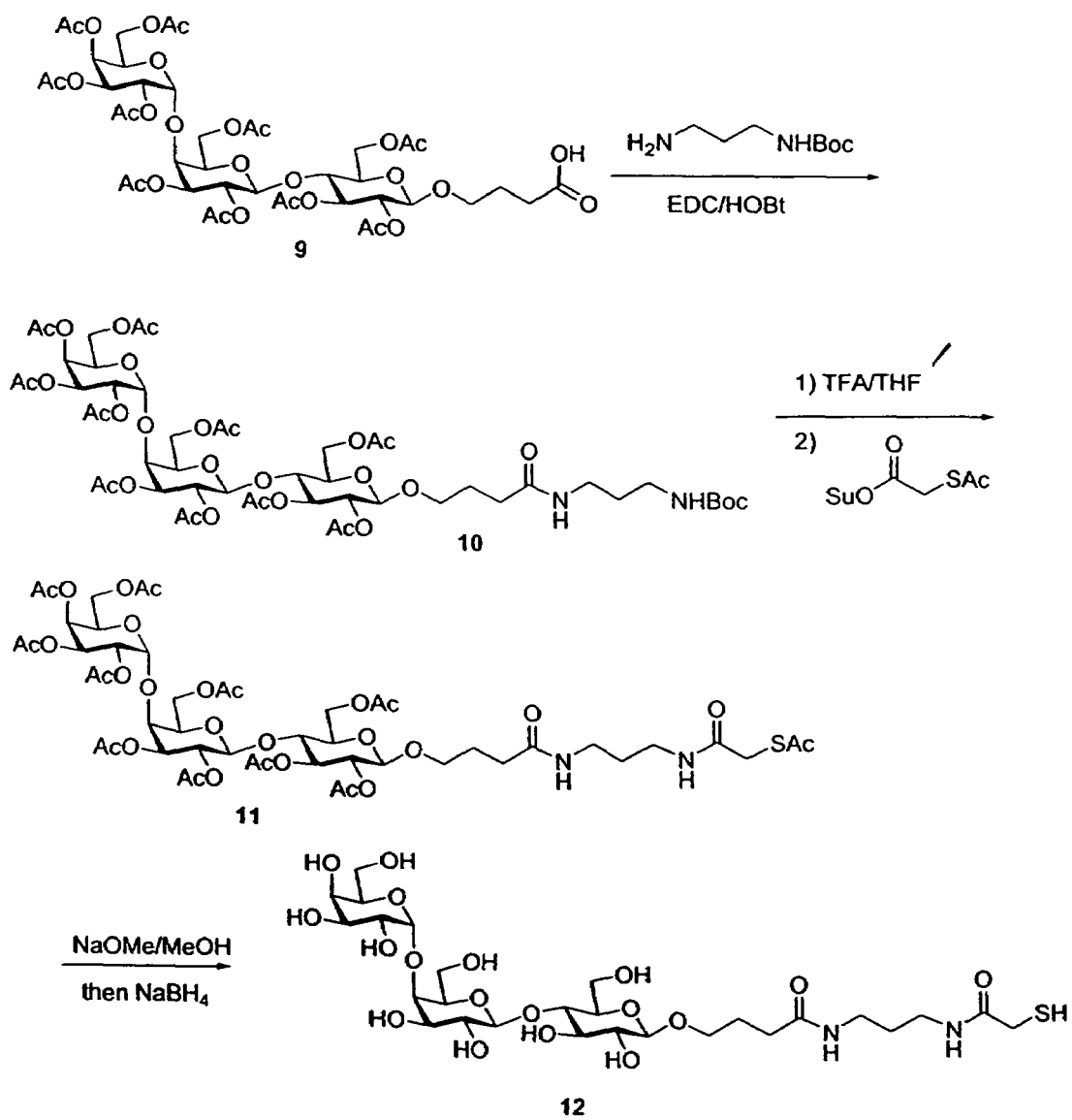

This example describes one method for synthesizing thiolated pK antigen, and the generation of pK antigen encapsulated gold nanoparticles. The synthesis of thiolated pK antigen is depicted in FIG. 8, which shows the various synthesis steps that can be taken starting with lactose octaacetate (Compound 1, shown in FIG. 8) available from Glycon Biochemicals GmbH.

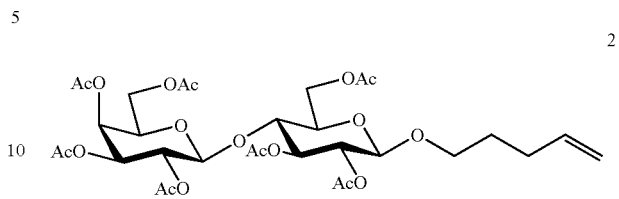

Compound 2, shown above and in FIG. 8, may be synthesized as described below. Thirty-three (33) % HBr in AcOH may be added dropwise over a period of 60 minutes to a cooled (ice bath) suspension of lactose octaacetate 1 (e.g., 10 g, 14.78 mmol), the reaction mixture may then be stirred for 4 hours and the ice bath removed. The solution is then diluted with $H_2O$ and extracted with $CH_2Cl_2$. The organic extracts are washed with $H_2O$, saturated in $NaHCO_3$, dried over $MgSO4$, and concentrated. The product is azeotroped with anhydrous toluene and dried under high vacuum to the lactosyl bromide (expected yield of about 96%) which may then be used without further purification.

Next, n-pentyl alcohol (5.0 equiv) is added to a suspension of $Ag_2CO_3$ (10 g, 14.78 mmol), freshly activated drierite (10 g) in $CH_2Cl_2$ (50 mL), and then the lactosyl bromide (9.88 g, 14.14 mmol). After the solution is stirred in the dark at room temperature for 16 h, the reaction is filtered through a plug of Celite with additional $CH_2Cl_2$ and concentrated to a yellow oil which is purified by flash column chromatography (50% EtOAc/Hexanes) to yield the pentenyl lactoside as a white foam (e.g., with a 70% yield).

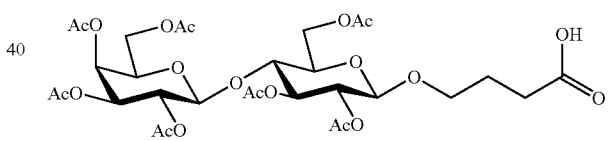

Compound 3, shown above and in FIG. 8, may be synthesized as follows. NaIO4 (604 mg, 2,825 mmol) and RuCl3 (29.3 mg, 141 umol) are added to a vigorously stirred solution of 2 (497.3 mg, 701 umol) in $CH_2Cl_2$—MeCN—$H_2O$ 2:2:3. After 2 hours an additional amount of NaIO4 (1 mmol) is added, and the stirring is continued for 2 hours. The mixture is then diluted with $H_2O$ and extracted with $CH_2Cl_2$. The combined organic phases is dried, filtered, and concentrated. Flash column chromatography gives 3 as a white foam (e.g. with an 85% yield).

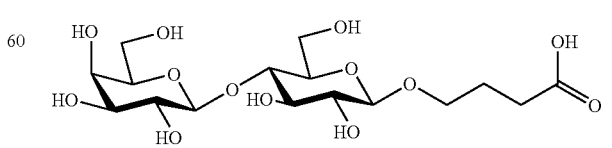

Compound 4, shown above and in FIG. 8, may be synthesized as follows. Compound 3 (1.9 g, 2.629 mmol) is dissolved in anhydrous MeOH (10 mL) and NaOMe (42.61 mg, 0.789 mmol) is added. The reaction is stirred at room temperature for 16 hours and neutralized with H+ resin. The reaction is filtered with additional MeOH and concentrated to a white solid 4 which may be used without further purification.

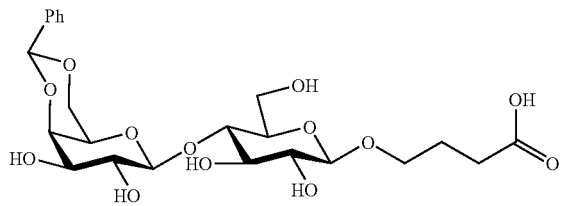

Compound 5, shown above and in FIG. 8, may be synthesized as follows. Compound 4 (0.91 g, 2,120 mmol) is dissolved in acetonitrile and DMF (5:2, 7 mL), and benzaldehyde dimethylacetal (0.83 mL, 5.513 mmol) and camphorsulfonic acid (CSA) (24 mg, 106 umol) is added. After stirring for 16 hours at room temperature, the mixture is diluted with CH$_2$Cl$_2$ and washed with saturated NaHCO$_3$. The organic mixture is dried with MgSO4, concentrated, and following the addition of ether (20 mL) to the resulting residue, pure 5, is recovered by filtration (e.g., 70% yield).

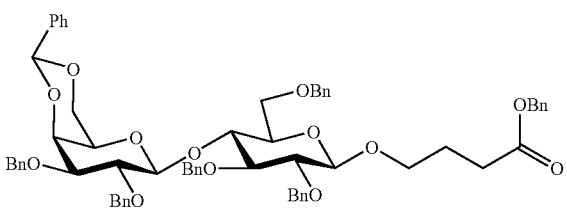

Compound 6, shown above and in FIG. 8, may be synthesized as follows. Compound 5 (1.0 g) and Et$_4$N (144 mg, 390 umol) are dried (azeotropic distillation with toluene), dissolved in DMF (20 mL) and cooled to 0 degrees Celsius. Benzyl bromide (2.78 mL, 23.41 mmol) is added followed by NaH (351 mg, 14.63 mmol) and the mixture is allowed to warm to room temperature over 14 hours. The mixture is diluted with EtOAc, washed with water, the organic layer is dried (MgSO$_4$) and evaporated. Purification of the residue by chromatography on silica gel gives pure 6 as a white solid (e.g. 70% yield).

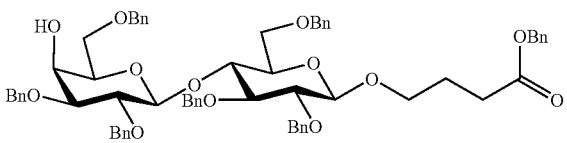

Compound 7, shown above and in FIG. 8, may be synthesized as follows. Compound 6 is dried (azeotropic distillation with toluene), and stored under vacuum for 15 hours prior to use. To a solution of 6 in CH$_2$Cl$_2$ at −78 degrees Celsius is added Et3SiH and BF3 OEt2. The reaction is stirred at −78 degrees for 6 hours. Saturated NaHCO$_3$, is added and the solution is extracted with CH$_2$Cl$_2$. The organic layer is dried over MgSO4, and concentrated. Purification of the residue by chromatography on silica gel gives pure 7 as a white solid.

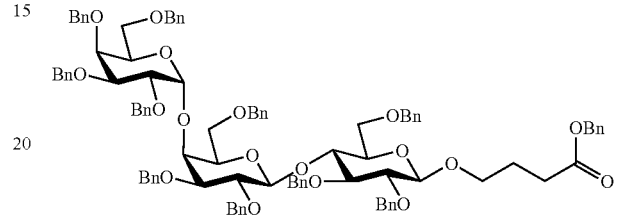

Compound 8, shown above and in FIG. 8, may be synthesized as follows. Trifluoromethanesulfonic anhydride (34 uL, 1.5 equiv) is added to a solution of galactose, 2,4,6-tri-tert-butylpyridine (151 mg, 0.61 mmol, 4.5equiv), and dimethyl sulfide (20 uL, 0.27 mmol, 2 equiv) in dichloromethane (1 mL) at −45 degrees Celsius. The resulting mixture is stirred at this temperature for 1 hour, then at 0 degrees for 15 minutes, and finally at 20 degrees for 15 minutes. A solution of 7 (1 equiv) in CH$_2$Cl$_2$ (1 mL) is then added via cannula. The resulting solution is stirred at 20 degrees for 24 hours. The reaction mixture is diluted with CH$_2$Cl$_2$ (10 mL) and washed sequentially with saturated NaHCO$_3$. The organic layer is dried over MgSO4, and concentrated. Purification of the residue by chromatography on silica gel gives pure 8 as a white solid.

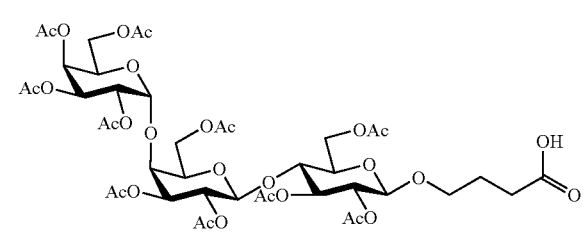

Compound 9, shown above and in FIG. 8, may be synthesized as follows. The solution of 8 is degassed with argon for 20 minutes before the addition of 10% Pd/C (5 mol, 12.1 mg). The vessel is pressurized to 90 psi of H$_2$ and stirred vigorously for 15 hours. The reaction is filtered through Celite and concentrated and may be used without further purification. Then pyridine is added Ac$_2$O (12 equiv). The reaction is stirred for 15 hours, diluted with CH$_2$Cl$_2$, and washed with 1N HCl and saturated NaHCO$_3$. Purification of the residue by chromatography on silica gel gives 9.

*Compound 10*

Compound 10, shown above and in FIG. 8, may be synthesized as follows. Compound 9 and 4-t-butyloxycarbonylaminopropylamine are dissolved in $CH_2Cl_2$ under ice bath, then, EDC is added and the reaction solution is warmed to room temperature and stirred for 48 hours. The reaction suspension is diluted with $CHCl_3$ and washed with $d-H_2O$ and saturated NaCl solution three times, and the combined organic layer is extracted with $CHCl_3$ two times. The organic layer is collected, dried over $MgSO_4$, filtered, and condensed to give a white solid. The solid is further purified by column chromatography to obtain compound 10.

*Compound 11*

Compound 11, shown above and in FIG. 8, may be synthesized as follows. Compound 10 is added to a solution of 50% TFA in $CH_2Cl_2$ at 0° C., gently warmed to room temperature, and stirred for 1.5 hours. After volatile components are removed in vacuo, the residue is added to $Et_3N$ and condensed two times to afford a crude product. To the solution of free-amine in $CH_2Cl_2$, acetylsulfanyl-acetic acid 2,5-dioxo-pyrrolidin-1-yl ester and $Et_3N$ is added at 0° C., the reaction mixture is stirred at 0° C. for 2 hours. The reaction solution is washed with brine three times, the organic layer is dried over $MgSO_4$, filtered, and concentrated to give residue. It is further purified by column chromatography to give the desired compound 11.

*Compound 12*

Compound 12, shown above and in FIG. 8, may be synthesized as follows. Compound 11 is treated with NaOMe in MeOH and stirred at room temperature overnight. This suspension is neutralized with Dowex 50WX8 to pH 6. The filtrate is collected by filtration and then is condensed to give a solid. The solid is dissolved in MeOH again and treated with $NaBH_4$ to reduce disulfide bond. After 1 hour stirring, the solution is quenched with Dowex 50WX8, filtered to collect the filtrate, and evaporated to afford compound 12 (thiolated pK antigen).

The thiolated pK antigen may then be used to generate pK antigen encapsulated gold nanoparticles as described in Example 4. For example, the compound 12 of this example may be substituted for Compound 4 in Example 4 in order to generate pK antigen encapsulated gold nanoparticles.

Example 9

Testing pK Antigen Encapsulated Gold Partiles

This example describes certain methods that can be employed to test the Shiga-like toxin binding and neutralizing properties of the Pk antigen encapsulated nanoparticles described in Example 8. These methods are taken from Kitov et al., Nature, 403:669-672, which is herein incorporated by reference.

One type of binding assay that can be performed is as follows. SLT-I dissolved in PBS (100 µl; 2.5 µg ml−1) may be coated on a 96-well ELISA plates (18 h at 4° C.). The plate is then washed five times with PBST (PBS containing Tween 20, 0.05% v/v), blocked for 1 h with milk (DIFCO, 2.5% in PBS, 100 µl). The plate is washed twice with PBST. Pk encapsulated nanoparticles may be mixed with inhibitor at concentrations in the range 0.1 nM to 10 mM, and the mixture (100 µl) added to the coated microtitre plate and incubated at room temperature (18 h). The plate is then washed five times with PBST and streptavidin horseradish peroxidase conjugate (100 μl) is added and incubated for 1 hour at room temperature. The plate is washed five times with PBST, 3,3', 5,5'-tetramethylbenzidine (TMB, 100 μl), and after 2 min the color reaction is stopped by the addition of 1 M phosphoric acid (100 μl). Absorbance is measured at 450 nm and the percentage inhibition is calculated using wells containing no inhibitor as the reference point.

The following cytotoxicity assay may be performed to evaluate the performance of the Pk antigen encapsulated nanoparticles described in Example 8. Pk antigen encapsulated nanoparticles (inhibitor) dissolved in double-distilled, deionized water. Stock solutions of purified SLT-I and SLT-II are prepared at concentrations of 400 ng ml−1 and 2 μg ml−1, respectively, in unsupplemented MEM. Serial dilutions, in unsupplemented MEM, of inhibitor solution are prepared using a 96-well microtitre plate. Next, 5 μl of stock SLT-I or SLT-II solution are added to each well (to 80 μl final volume) of the appropriate rows in the dilution plate. The solution in each of the dilution plate wells is thoroughly mixed and the microtitre plate is incubated for 1 h at 37° C., after which 20 μl from each well is transferred to the corresponding well of a 96-well microtitre plate containing confluent Vero cell monolayers and 200 μl of MEM supplemented with fetal bovine serum. The Vero cell microtitre plate is incubated for an additional 48 h in a 37° C. incubator in an atmosphere of 5% CO2/95% air. The Vero cell monolayers are then fixed with methanol and cytotoxicity is measured as described in Armstrong et al., J. Infect. Dis. 164:1160-67 (1991), herein incorporated by reference.

The above assays, or similar assays (or assays similar to those described in Kitov et al. J. Chem. Soc.-Perkin Trans. 1, 2001, Iss 8, pp 838-853, herein incorporated by reference) may be used to test and verify the SLT (I and II) binding and neutralizing properties of the Pk antigen encapsulated nanoparticles described in Example 8. Additional animal model assays may then be employed using the Pk antigen encapsulated nanoparticles described above, for example, to determine a therapeutic dose that could be used to neutralize SLT intoxication in an animal (e.g. mouse, human, etc).

Example 10

Synthesis of Carbohydrate-Encapsulated Gold Nanoparticles

This example describes the synthesis of various carbohydrate-encapsulated gold nanoparticles (carbohydrate-AuNP). These carbohydrate-AuNP are shown in Table 3 below. While the detailed procedures are described below, briefly, nearly mon-dispersed gold nanoparticles with average diameters of 6 or 20 nm were prepared, and their sizes were confirmed using transmission electron microscopy. Various carbohydrate ligands with different linker lengths were synthesized with an S—H group at one side, which was then linked to the nanoparicles through the formation of a strong thiol bond. The amount of carbohydrates attached on each gold nanoparticle was quantitatively determined by $H_2SO_4$/phenol assay and elemental analysis (6-m-AuNP, s- and 1-20-m-AuNP had on average 200, 680, and 840 mannose ligands, respectively, clustered on the nanoparticle surface).

A. Synthetic Schemes and NMR Data:

Synthesis of 6-g-AuNP

TABLE 3

| Sugar | R | Particle size | Abbreviation |
|---|---|---|---|
| Mannose | \O(CH2)2S— | 6 nm | 6-m-AuNP |
| Mannose | \O(CH2)2S— | 20 nm | s-20-m-AuNP |
| Mannose | \O(CH2)2(OCH2CH2)4S— | 20 nm | l-20-m-AuNP |
| Glucose | \O(CH2)2S— | 6 nm | 6-g-AuNP |
| Galactose | \O(CH2)2S— | 6 nm | 6-t-AuNP |

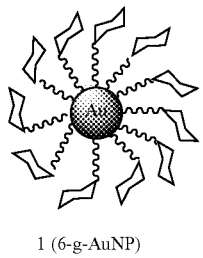

1 (6-g-AuNP)

Keys: (a) HBr/HOAc, 84%. (b) 4-pentenyl alcohol, Hg(CN)$_2$, 87% (c) HSAc, AIBN, dioxane, 95%. (d) NaOMe(cat.), MeOH, 93%. (e) HAuCl$_4$, NaBH$_4$.

5-Thiopentyl β-D-glucopyranoside dimmer (3). $^1$HNMR (400 MHz, CD$_3$OD) δ 1.50-1.55 (m, 2H), 1.62-1.69 (m, 4H), 2.51 (t, J=7.8 Hz, 2H), 3.17 (dd, J=8.8, 7.8 Hz, 1H), 3.33-3.35 (m, 3H), 3.56-3.59 (m, 1H), 3.70 (dd, J=11.8, 5.3 Hz, 1H), 3.87 (m, 2H), 4.26 (d, J=7.8 Hz, 1H); $^{13}$CNMR (100 MHz, CD$_3$OD) δ 25.04, 26.00, 30.38, 35.14, 62.97, 70.80, 71.86, 75.30, 78.08, 78.31, 104.54.

Synthesis of 6-t-AuNP

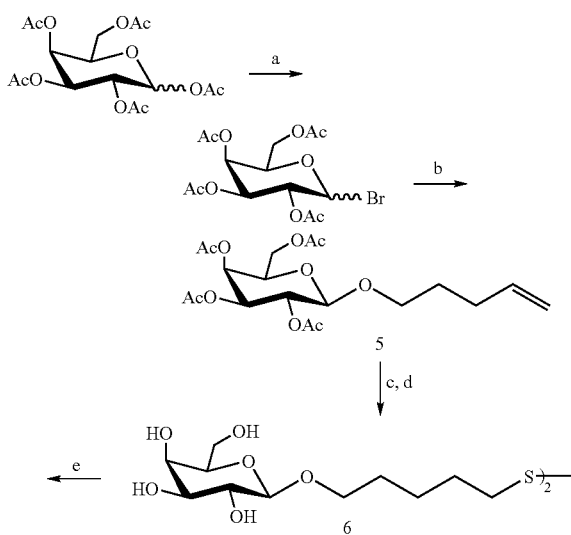

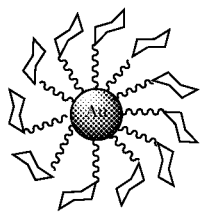

4 (6-t-AuNP)

Keys: (a) HBr/HOAc, 85%. (b) 4-pentenyl alcohol, Hg(CN)$_2$, 80% (c) HSAc, AIBN, dioxane, 95%. (d) NaOMe(cat.), MeOH, 90%. (e) HAuCl$_4$, NaBH$_4$.

5-Thiopentyl β-D-galactopyranoside dimmer (4). $^1$HNMR (400 MHz, CHCl$_3$) δ 1.50-1.55 (m, 2H), 2.72 (t, J=7.3 Hz, 2H), 3.43-3.47 (m, 1H), 3.52-3.65 (m, 17H), 3.63 (t, J=9.6 Hz, 1H), 3.70-3.78 (m, 3H), 3.81 (dd, J=3.3, 1.7 Hz, 1H), 3.84 (dd, J=11.7, 2.4 Hz, 1H), 4.76 (d, J=1.6 Hz, 1H); $^{13}$CNMR (400 MHz, CHCl$_3$) δ 24.66, 24.74, 29.27, 33.61, 62.83, 71.48, 72.46, 72.72, 77.88, 78.34, 98.85.

Synthesis of l-20-m-AuNP

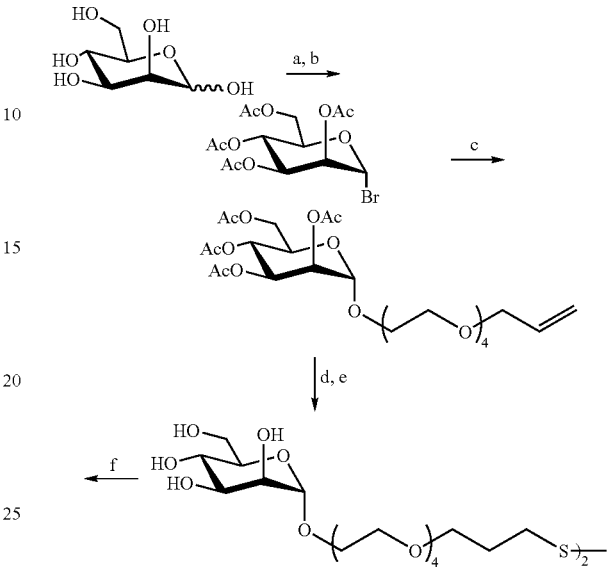

l-20-m-AuNP

Keys: (a) Ac$_2$O, I$_2$, 90%. (b) HBr/HOAc, 80%. (c) 2-{2-[2-(2-allyloxy-ethoxy)-ethoxy]-ethoxy}-ethanol, Hg(CN)$_2$, 28% (d) HSAc, AIBN, dioxane, 74%. (e) NaOMe(cat.), MeOH, 83%. (f) HAuCl$_4$, Reducing reagent tPEG 2,3,4,6-tetra-O-acetyl-α-D-mannopyranoside (8). $^1$HNMR (400 MHz, CHCl$_3$) δ 2.01 (s, 3H), 2.04 (s, 3H), 2.10 (s, 3H), 2.15 (s, 3H), 3.47 (dt, J=11.2, 6.4 Hz, 1H), 3.52-3.65 (m, 16H), 3.70 (dt, J=11.2, 6.4 Hz, 1H), 3.96 (d, J=5.7, 1.2 Hz, 1H), 3.99 (ddd, J=10.0, 5.2, 2.8 Hz, 1H), 4.11 (dd, J=12.0, 2.8 Hz, 1H), 4.27 (dd, J=12.0, 5.2 Hz, 1H), 4.80 (d, J=1.6 Hz, 1H), 4.98-5.08 (m, 2H), 5.18 (dd, J=10.7, 1.7 Hz, 1H), 5.27 (dd, J=17.2, 1.7 Hz, 1H), 5.81-5.85 (m, 1H); $^{13}$CNMR (100 MHz, CHCl$_3$) δ 20.68, 20.70, 20.89, 20.93, 62.53, 62.63, 63.64, 66.25, 65.68, 68.37, 68.86, 69.09, 69.37, 70.18, 70.53, 70.58, 71.16, 72.20, 92.11, 117.19, 134.66, 169.86, 170.09, 170.26, 170.90.

Thio-tPEG 2,3,4,6-tetra-O-acetyl-α-D-mannopyranoside. $^1$HNMR (400 MHz, CHCl$_3$) δ 1.14-1.47 (m, 2H), 2.01 (s, 3H), 2.04 (s, 3H), 2.10 (s, 3H), 2.15 (s, 3H), 2.34 (s, 3H), 2.89 (t, J=7.2 Hz, 2H), 3.47 (dt, J=11.2, 6.4 Hz, 1H), 3.52-3.65 (m, 18H), 3.70 (dt, J=11.2, 6.4 Hz, 1H), 3.96 (d, J=5.7, 1.2 Hz, 1H), 3.99 (ddd, J=10.0, 5.2, 2.8 Hz, 1H), 4.11 (dd, J=12.0, 2.8 Hz, 1H), 4.27 (dd, J=12.0, 5.2 Hz, 1H), 4.80 (d, J=1.6 Hz, 1H), 4.98-5.08 (m, 2H); $^{13}$CNMR (100 MHz, CHCl$_3$) δ 20.68, 20.70, 20.74, 20.93, 24.37, 62.53, 62.63, 63.64, 65.68, 66.25, 68.37, 68.86, 69.09, 69.37, 70.18, 70.53, 70.58, 71.16, 72.20, 92.11, 169.86, 170.09, 170.26, 170.90, 192.13.

tPEG α-D-mannopyranoside dimmer (9). $^1$HNMR (400 MHz, CD$_3$OD) δ 1.50-1.55 (m, 2H), 2.72 (t, J=7.3 Hz, 2H), 3.43-3.47 (m, 1H), 3.52-3.65 (m, 17H), 3.63 (t, J=9.6 Hz, 1H), 3.70-3.78 (m, 3H), 3.81 (dd, J=3.3, 1.7 Hz, 1H), 3.84 (dd, J=11.7, 2.4 Hz, 1H), 4.76 (d, J=1.6 Hz, 1H); $^{13}$CNMR (400 MHz, CD$_3$OD) δ 24.68, 24.70, 33.74, 63.53, 63.63, 65.64, 66.68, 67.25, 69.37, 69.86, 70.09, 70.37, 71.18, 72.53, 72.58, 74.16, 75.20, 100.11.

B. Synthesis of Carbohydrate-Encapsulated Gold Nanoparticles.

An HAuCl$_4$ aqueous solution was added to a toluene solution in the presence of tetraoctylammonium bromide at room temperature. After stirring for 1 min, the organic layer was collected. The organic layer was then mixed with a freshly prepared reducing agent and methanol solution of carbohydrates (manno-, gluco- or galactopyranosides) with vigorous stirring. After stirring for 1 h, carbohydrate-AuNP were precipitated by centrifugation and then washed with methanol. The diameters of gold nanoparticles were controlled by reaction temperature and type of surfactant (see Brust et al., J. Chem. Soc. Chem. Commun., 1994, 801-802, herein incorporated by reference).

Example 11

Concanavallin A Binding Affinity Assays

Figure 9:
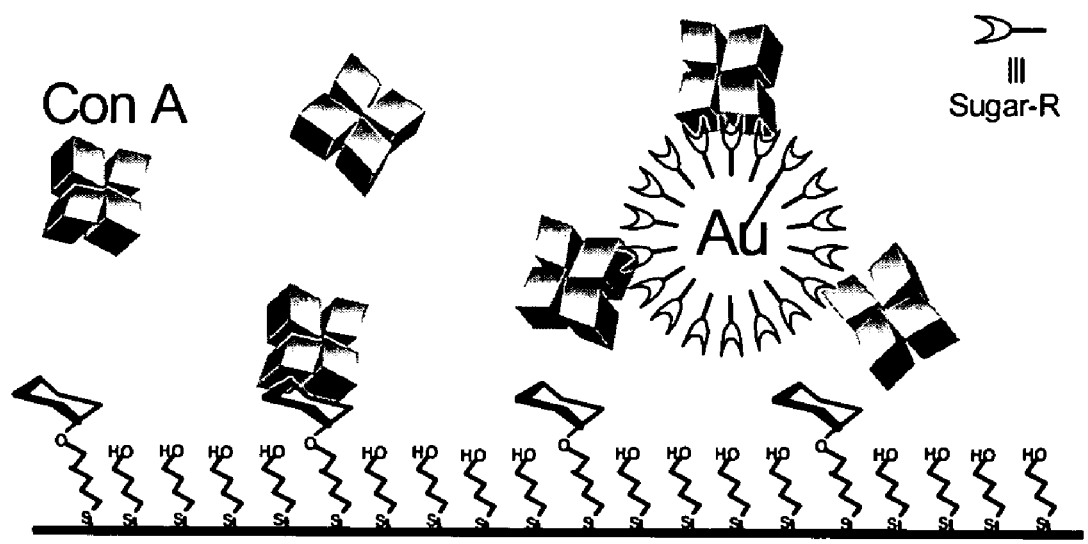
FIG. 9 shows a schematic illustration of the interactions of carbohydrate-AuNP and Con A on a biosensor chip composed of mannopyranoside and thiobutanol.

To assess the binding affinity of α-D-methyl-mannopyrannoside (α MeMan) and various carbohydrate-AuNP for Con A, an SPR competition binding assay was employed based on previous reports (See Mann et al., J. Am. Chem. Soc. 1998, 120:10575; and Nieba et al., Anal. Biochem., 1996, 234:155; herein incorporated by reference) with certain modifications. A self-assembled monolayer composed of 20% mannopyranoside ligand and 80% thiobutanol mixture was generated on a J1 biosensor chip (See FIG. 9). In particular, immobilization of ligand to the biosensor chip was preformed in BIAcore 3000 instrument. A mixture of 4-mercapto-1-butanol (Ligand A) and 5-thiopentyl α-D-mannopyranoside (Ligand B) in deionized water was injected into a flow cell with the J1 biochip. The mixtures of Ligand A and Ligand B with various ratios were tested to generate the chips with considerably higher affinity to Con A. It was found that, the Con A tetramer displayed a good binding profile with characteristic association, equilibrium, and dissociation phases, when the mixture with the ratio of 4:1 (Ligand A/B) were applied.

Figure 10:
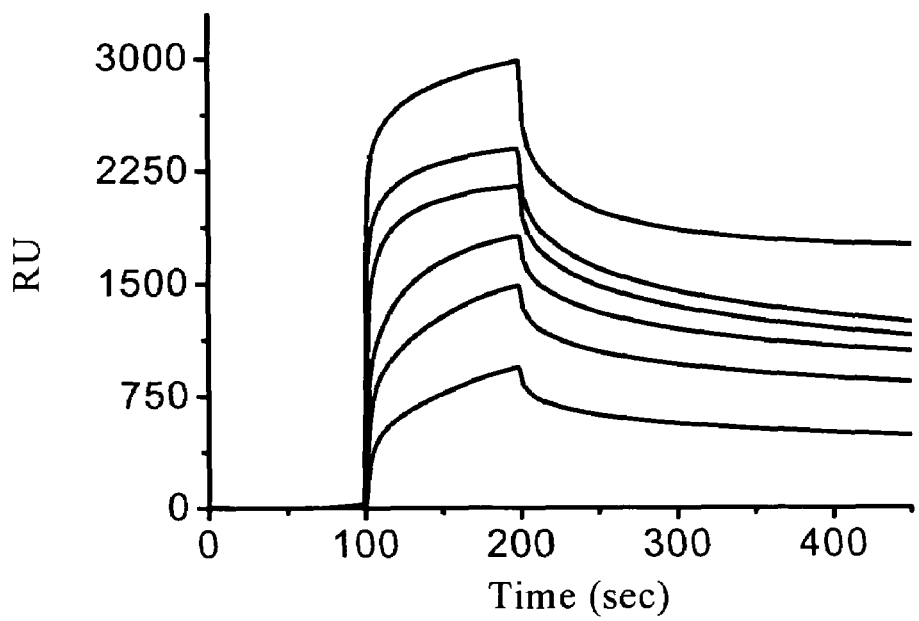
FIG. 10A shows a set of SPR response curves obtained after different concentrations of Con A solution were applied to a biosensor chip as described in Example 11.
FIG. 10B shows a set of SPR response curves obtained after difference concentrations of α MeMan were applied to a biosensor chip as described in Example 11.
Figure 10:
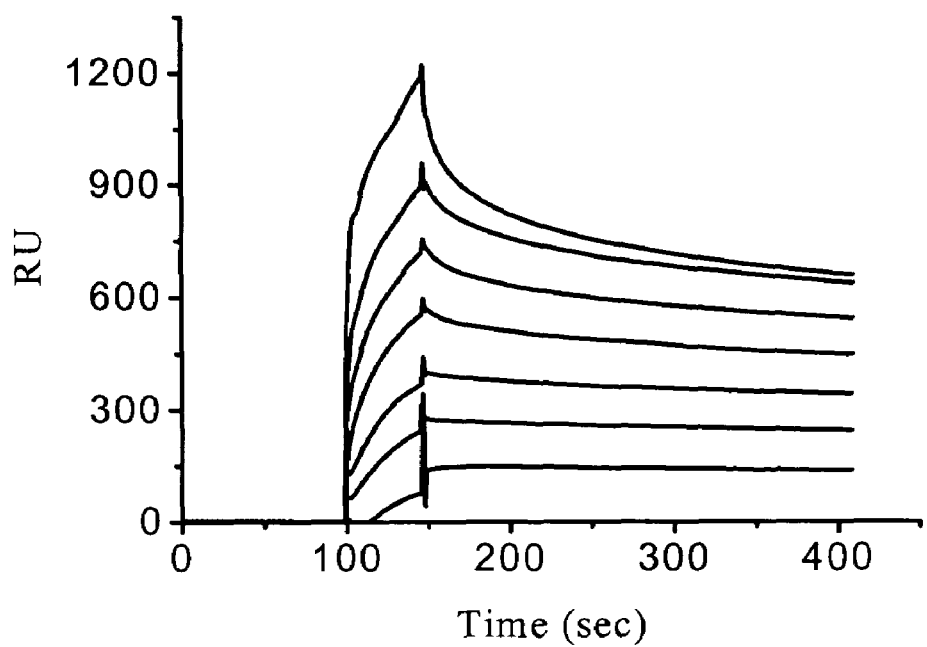

Next, the binding affinity of Con A for this chip was determined by titration with a series of Con A concentrations to generate multiple SPR curves. In particular, Con A was dissolved in sample buffer (1.0 mL, 20 mM HEPES, pH 7.0, 90 mM NaCl with 1 mM MnCl$_2$ and CaCl$_2$) and then filtered by a syringe. Con A solution (50 μL) was injected over immobilized biosensor surface and allowed 260 seconds for dissociation and then followed by regeneration buffer. A set of SPR response curves was obtained after different concentrations of Con A solution were applied (See FIG. 10A, showing curves for 6, 3, 1.5, 0.38, 0.19 uM of Con A (top to bottom)). Using the rectangular hyperbolic equation, the association constant K$_a$ of Con A for this chip was obtained, and the value was 7.95×10$^6$ M$^{-1}$.

Figure 11:
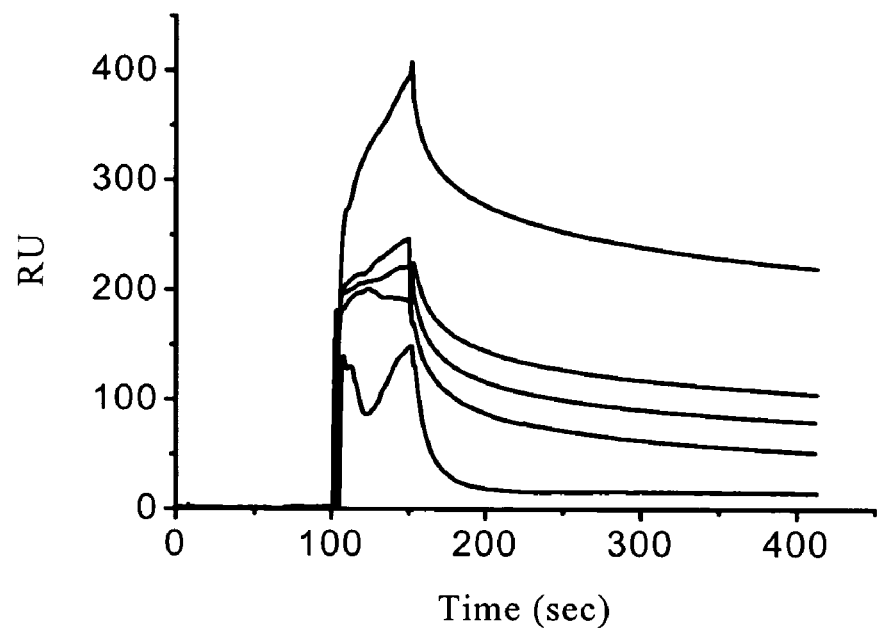
FIG. 11A shows a set of inhibition curves after different concentrations of 20-1-m-AuNP were applied to a biosensor chip in the presence of 0.5 uM Con A as described in Example 11.
FIG. 11B shows a set of inhibition curves after different concentrations of 6-m-AuNP were applied to a biosensor chip in the presence of 0.5 uM Con A as described in Example 11.
Figure 11:
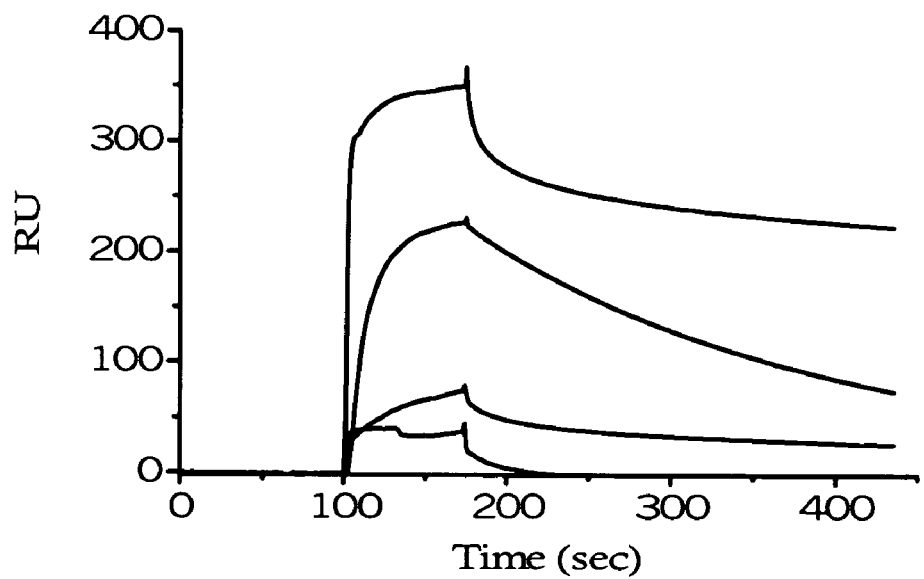

Competition assays were then conducted. Con A tetramer (0.5 uM) was first mixed with the inhibitor (α MeMan, 6-m-AuNP, s-20-m-AuNP, 1-20-m-AuNP, 6-g-AuNP or 6-t-AuNP) and then the resulting mixture was pre-incubated for 1 hr before the injection. The mixture (50 uL) was then injected and the flow rate was controlled at 60 uL/minute. The equilibrium binding response values was collected at equilibrium binding portion of the curve (260 seconds post-injection). Various SPR response curves were obtained after different concentrations of the inhibitor solution were applied. FIG. 10B shows a set of inhibition curves for 0, 0.875, 1.75, 3.5, 7, 14, 28 mM of a MeMan (top to bottom); FIG. 11A shows a set of inhibitions curves for 0, 0.006, 0.050, 0.101, 0.202 uM of 20-1-m-AuNP (top to bottom); and FIG. 11B shows a set of inhibition curves for 0, 0.175, 0.5 and 1 uM 6-m-AuNP (top to bottom). K$_i$ values were determined by fitting the data into the equation: f=[I]/([I]+K$_i$ (1+F/K$_d$)). From the inhibition curves of each carbohydrate-AuNP, its inhibition constant (Ki) is obtained using the equations derived by Attie et al., J. Chem. Educ., 1995, 72:119. These values are shown in Table 4 below. Also, to compare the inhibition potencies of the individual mannose ligand on three different mannose-AuNP, with respect to monovalent α MeMan, the relative inhibition potency (RIP) was calculated (shown in Table 4).

TABLE 4

| Compound | K$_i$ | RIP |
| --- | --- | --- |
| α MeMan | 20 · 10$^{-4}$ | 1.0 |
| 6-m-AuNP | 8.8 · 10$^{-8}$ | 11.2 |
| s-20-m-AuNP | 2.3 · 10$^{-9}$ | 127.8 |
| 1-20-m-AuNP | 3.5 · 10$^{-9}$ | 67.5 |
| 6-g-AuNP | 1.6 · 10$^{-7}$ | □ |
| 6-t-AuNP | — | — |

— no inhibition;
/ not determined

The RIP values for the mannose ligands of three m-AuNP are from 11 to 128 (Table 4), indicating that the multivalent mannose ligands of these m-AuNP have one to two orders higher affinities to Con A than monovalent mannose ligands. In addition, all three m-AuNP exhibited a stronger inhibition effect than 6-g-AuNP and 6-t-AuNP. 6-t-AuNP displayed no detectable inhibition effect. This is consistent with the previous studies that Con A binds to mannose better than glucose but does not bind to galactose. Therefore, no switch of Con A specificity for carbohydrates clustered on nanoparticles was observed in our system. Taken together, these results demonstrate that clustering of carbohydrate ligands on a nanoparticle significantly enhances the ligand binding affinity for lectins, with no change in lectin binding specificity.

It has been studied that the Con A tetramer presents two saccharide binding sites on each face, and the distance between them is 6.5 nm (See, Derewenda et al., EMBO, J., 1989, 8:2189). The inhibition potencies of 6-m-AuNP and 20-m-AuNP in the SPR competition assays (Table 1) were compared. As the particle diameters of 6-m-AuNP and 20-m-AuNP are comparable to or significantly larger than the distance between two relevant binding sites on Con A, respectively, the mannose ligands of 6-m-AuNP are less favorable to engage in the divalent binding of a Con A tetramer than those of 20-m-AuNP. The nanoparticles described above showed that the carbohydrate ligands with ability to span the requisite distance to occupy two Con A saccharide binding sites are more effective multivalent inhibitors than those fail to engage divalent binding. The above example demonstrates that a nanoparticle can be a good multivalent ligand carrier. The multivalent interactions between m-AuNP and Con A are affected by nanoparticle size and the linker of mannose ligands.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A saccharide-conjugated nanoparticle comprising:
   (a) a core gold nanoparticle, comprising gold atoms, without Fe atoms and having no magnetic property;
   (b) a plurality of saccharide molecules; and
   (c) a linker, linking the plurality of saccharide molecules to the core gold nanoparticle;
   wherein the saccharide-conjugated nanoparticle has an average diameter of about 2-9 nm, and
   wherein the linker is 5-thio-pentan-1-ol.

2. The saccharide-conjugated nanoparticle of claim 1, wherein the plurality of saccharide molecules are selected from the group consisting of a monosaccharide and a Pk antigen.

3. The saccharide conjugated nanoparticle of claim 1, wherein the plurality of saccharide molecules comprises at least 150 molecules.

4. A composition comprising:
   (a) a saccharide-conjugated nanoparticle, which comprises:
      (i) a core gold nanoparticle, comprising gold atoms, without Fe atoms and having no magnetic property;
      (ii) a plurality of saccharide molecules; and
      (iii) a linker, attaching the plurality of saccharide molecules to the core gold nanoparticle; and
   (b) a pathogen, bound to the saccharide-conjugated nanoparticle;
   wherein the linker is 5-thio-pentan-1-ol.

5. The composition of claim 4, wherein the pathogen is selected from the group consisting of bacteria, viruses, mycoplasma and fungi.

6. The composition of claim 4, wherein the plurality of saccharide molecules are selected from the group consisting of a monosaccharide, and a Pk antigen.

7. The composition of claim 4, wherein the plurality of saccharide molecules comprise at least 150 molecules.

8. The composition of claim 6, wherein the monosaccharide is selected from the group consisting of mannose, galactose, and glucose.

9. The composition of claim 6, wherein the plurality of saccharide molecules are Pk antigen.

10. The composition of claim 6, wherein the plurality of saccharide molecules comprise at least 150 molecules.

11. A saccharide-conjugated nanoparticle comprising:
    (a) a core gold nanoparticle, comprising gold atoms, without Fe atoms and having no magnetic property;
    (b) a plurality of saccharide molecules; and
    (c) a linker, attaching the plurality of saccharide molecules to the core gold nanoparticle;
    wherein the plurality of saccharide molecules are selected from the group consisting of a monosaccharide and a Pk antigen, and wherein the linker is 5-thio-pentan-1-ol.

12. The saccharide-conjugated nanoparticle of claim 11, wherein the plurality of saccharide molecules comprises at least 150 molecules.

13. The saccharide-conjugated nanoparticle of claim 11, wherein the monosaccaride is selected from the group consisting of mannose, galactose and glucose.

14. A composition comprising:
    (a) a saccharide-conjugated nanoparticle according to claim 11; and
    (b) a pathogen, bound to the nanoparticle.

15. The composition of claim 14, wherein the monosaccharide is selected from the group consisting of mannose, galactose, and glucose.

* * * * *